(12) United States Patent
Noy et al.

(10) Patent No.: US 11,439,708 B2
(45) Date of Patent: Sep. 13, 2022

(54) NANOTUBE TRANS-MEMBRANE CHANNELS MIMICKING BIOLOGICAL PORINS

(71) Applicants: LAWRENCE LIVERMORE NATIONAL SECURITY, LLC, Livermore, CA (US); The Regents of the University of California, Oakland, CA (US); UNIVERSIDAD DEL PAÍS VASCO, Vizcaya (ES)

(72) Inventors: Aleksandr Noy, San Carlos, CA (US); Jia Geng, Henan (CN); Jianfei Zhang, Merced, CA (US); Vadim Frolov, Vizcaya (ES)

(73) Assignees: LAWRENCE LIVERMORE NATIONAL SECURITY, LLC, Livermore, CA (US); THE REGENTS OF THE UNIVERSITY OF CALIFORNIA, Oakland, CA (US); UNIVERSIDAD DEL PAÍS VASCO, Vizcaya (ES)

( * ) Notice: Subject to any disclaimer, the term of this patent is extended or adjusted under 35 U.S.C. 154(b) by 0 days.

(21) Appl. No.: 15/503,983

(22) PCT Filed: Oct. 5, 2015

(86) PCT No.: PCT/US2015/054084
§ 371 (c)(1),
(2) Date: Feb. 14, 2017

(87) PCT Pub. No.: WO2016/057427
PCT Pub. Date: Apr. 14, 2016

(65) Prior Publication Data
US 2017/0304447 A1   Oct. 26, 2017

Related U.S. Application Data

(60) Provisional application No. 62/060,494, filed on Oct. 6, 2014.

(51) Int. Cl.
*A61K 47/02* (2006.01)
*C01G 39/06* (2006.01)
(Continued)

(52) U.S. Cl.
CPC .............. *A61K 47/02* (2013.01); *A01N 25/04* (2013.01); *A61K 9/0092* (2013.01); *A61K 9/1272* (2013.01); *B01J 13/08* (2013.01); *B01J 13/20* (2013.01); *B01J 13/203* (2013.01); *C01B 21/064* (2013.01); *C01B 32/17* (2017.08); *C01B 32/172* (2017.08); *C01B 32/174* (2017.08); *C01B 32/176* (2017.08); *C01G 39/06* (2013.01); *C12Q 1/6825* (2013.01); *C12Q 1/6869* (2013.01); *G01N 27/44791* (2013.01); *B82Y 5/00* (2013.01); *B82Y 15/00* (2013.01); *B82Y 40/00* (2013.01); *C01B 2202/02* (2013.01); *C01B 2202/34* (2013.01); *C01B 2202/36* (2013.01); *C01P 2004/04* (2013.01); *C01P 2004/13* (2013.01); *Y10S 977/746* (2013.01); *Y10S 977/75* (2013.01); *Y10S 977/847* (2013.01); *Y10S 977/907* (2013.01); *Y10S 977/915* (2013.01); *Y10S 977/924* (2013.01)

(58) Field of Classification Search
CPC ............ C12Q 1/6825; C12Q 2565/631; C12Q 1/6869; A01N 25/04; A61K 47/02; A61K 9/0092; A61K 9/1272; B01J 13/08; B01J 13/20; B01J 13/203; B82Y 15/00; B82Y 40/00; B82Y 5/00; C01B 21/064; C01B 2202/02; C01B 2202/34; C01B 2202/36; C01B 31/026; C01B 31/0266; C01B 31/0273; C01B 31/028; C01B 32/17; C01B 32/172; C01B 32/174; C01B 32/176; C01G 39/06; C01P 2004/04; C01P 2004/13; G01N 27/44791; Y10S 977/746; Y10S 977/75; Y10S 977/847; Y10S 977/907; Y10S 977/915; Y10S 977/924
USPC .......................................................... 424/450
See application file for complete search history.

(56) References Cited

U.S. PATENT DOCUMENTS 4,302,336 A   11/1981   Kawaguchi et al.
4,434,057 A   2/1984    Marquardt
(Continued)

FOREIGN PATENT DOCUMENTS

EP   0148551 A2 *  7/1985  ........... A61K 9/1277
EP   1 340 544 A1   9/2003
(Continued)

OTHER PUBLICATIONS

García-Fandiño et al. PNAS, (May 2012), vol. 19, No. 18, pp. 6939-6944. (Year: 2012).*
Shimizu et al. Nature, (Jun. 1999), vol. 399, pp. 483-487 (Year: 1999).*
Dutt et al., Current Nanoscience, 2011, 7, 699-715. (Year: 2011).*
Lacerda et al., Nanoscale, 2013, 5, 10242-10250. (Year: 2013).*
(Continued)

*Primary Examiner* — Janet L Epps-Smith
(74) *Attorney, Agent, or Firm* — Foley & Lardner LLP

(57) ABSTRACT

Provided herein is a nanopore structure, which in one aspect is a "carbon nanotube porin", that comprises a short nanotube with an associated lipid coating. Also disclosed are compositions and methods enabling the preparation of such nanotube/lipid complexes. Further disclosed is a method for therapeutics delivery that involves a drug delivery agent comprising a liposome with a NT loaded with a therapeutic agent, introducing the therapeutic agent into a cell or a tissue or an organism; and subsequent release of the therapeutic agents into a cell.

28 Claims, 13 Drawing Sheets
Specification includes a Sequence Listing.

(51) Int. Cl.
| | |
|---|---|
| C01B 21/064 | (2006.01) |
| C01B 32/174 | (2017.01) |
| C01B 32/176 | (2017.01) |
| C01B 32/17 | (2017.01) |
| C01B 32/172 | (2017.01) |
| A01N 25/04 | (2006.01) |
| A61K 9/00 | (2006.01) |
| A61K 9/127 | (2006.01) |
| B01J 13/08 | (2006.01) |
| B01J 13/20 | (2006.01) |
| G01N 27/447 | (2006.01) |
| B82Y 15/00 | (2011.01) |
| B82Y 5/00 | (2011.01) |
| B82Y 40/00 | (2011.01) |
| C12Q 1/6825 | (2018.01) |
| C12Q 1/6869 | (2018.01) |

(56) References Cited

U.S. PATENT DOCUMENTS

| | | | |
|---|---|---|---|
| 4,611,053 A | 9/1986 | Sasa | |
| 5,051,178 A | 9/1991 | Uemura et al. | |
| 5,102,550 A | 4/1992 | Pizzino et al. | |
| 5,376,253 A | 12/1994 | Rychen et al. | |
| 5,698,175 A | 12/1997 | Hiura et al. | |
| 6,337,018 B1 | 1/2002 | Mickols | |
| 6,824,689 B2 | 11/2004 | Wang et al. | |
| 6,858,197 B1 | 2/2005 | Delzeit | |
| 6,863,942 B2 | 3/2005 | Ren et al. | |
| 7,205,069 B2 | 4/2007 | Smalley et al. | |
| 7,211,320 B1 | 5/2007 | Cooper et al. | |
| 7,229,556 B1 | 6/2007 | Hinds et al. | |
| 7,290,667 B1 | 11/2007 | Bakajin et al. | |
| 7,301,191 B1 | 11/2007 | Tombler et al. | |
| 7,413,723 B2 | 8/2008 | Niu et al. | |
| 7,419,601 B2 | 9/2008 | Cooper et al. | |
| 7,439,731 B2 | 10/2008 | Crafts et al. | |
| 7,459,121 B2 | 12/2008 | Liang et al. | |
| 7,473,411 B2 | 1/2009 | Ajayan et al. | |
| 7,572,426 B2 | 8/2009 | Strano et al. | |
| 7,611,628 B1 | 11/2009 | Hinds, III | |
| 7,623,340 B1 | 11/2009 | Song et al. | |
| 7,931,838 B2 | 4/2011 | Marand et al. | |
| 7,993,524 B2* | 8/2011 | Ratto | B01D 69/12 210/652 |
| 8,029,856 B2 | 10/2011 | Miyoshi et al. | |
| 8,038,887 B2 | 10/2011 | Bakajin et al. | |
| 8,177,979 B2 | 5/2012 | Ratto et al. | |
| 8,196,756 B2 | 6/2012 | Ratto et al. | |
| 8,286,803 B2 | 10/2012 | Nowak et al. | |
| 8,541,322 B2 | 9/2013 | Barrera et al. | |
| 2003/0116503 A1 | 6/2003 | Wang et al. | |
| 2003/0121857 A1 | 7/2003 | Kurth et al. | |
| 2003/0165418 A1 | 9/2003 | Ajayan et al. | |
| 2004/0023372 A1 | 2/2004 | Klein et al. | |
| 2004/0173506 A1 | 9/2004 | Doktycz et al. | |
| 2005/0079379 A1 | 4/2005 | Wadsworth et al. | |
| 2006/0073089 A1 | 4/2006 | Ajayan et al. | |
| 2006/0275371 A1 | 12/2006 | Dai et al. | |
| 2007/0137701 A1 | 6/2007 | Sainte Catherine et al. | |
| 2008/0149561 A1 | 6/2008 | Chu et al. | |
| 2008/0290020 A1 | 11/2008 | Marand et al. | |
| 2009/0321355 A1 | 12/2009 | Ratto et al. | |
| 2010/0025330 A1 | 2/2010 | Ratto et al. | |
| 2010/0069606 A1* | 3/2010 | Bangera | B82Y 30/00 530/317 |
| 2010/0206811 A1 | 8/2010 | Ng et al. | |
| 2011/0220574 A1 | 9/2011 | Bakajin et al. | |
| 2011/0229529 A1 | 9/2011 | Irvine et al. | |
| 2011/0253630 A1 | 10/2011 | Bakajin et al. | |
| 2012/0080378 A1 | 4/2012 | Revanur et al. | |
| 2012/0080380 A1 | 4/2012 | Wang et al. | |
| 2012/0241371 A1 | 9/2012 | Revanur et al. | |
| 2012/0261620 A1 | 10/2012 | Richter et al. | |
| 2012/0285890 A1 | 11/2012 | Koehler et al. | |

FOREIGN PATENT DOCUMENTS

| | | |
|---|---|---|
| GB | 2 399 092 A | 9/2004 |
| WO | WO-2005/001021 A2 | 1/2005 |
| WO | WO-2005/069750 A2 | 8/2005 |
| WO | WO-2007/025104 A2 | 3/2007 |

OTHER PUBLICATIONS

Chakravarty, P. et al. (2008) "Thermal ablation of tumor cells with antibody-functionalized single-walled carbon nanotubes," PNAS 105(25):8697-8702.

Liu, Z. et al. (2009) "Preparation of carbon nanotube bioconjugates for biomedical applications," Nature Protocols 4(9):1372-1383.

Wallace, E.J. et al. (2009) "Carbon nanotube self-assembly with lipids and detergent: a molecular dynamics study," Nanotechnology 20:045101, 1-6.

International Preliminary Report on Patentability (IPEA/KR) in International Application No. PCT/US2015/054084, dated Jan. 24, 2017.

International Search Report and Written Opinion (ISA/KR) in International Application No. PCT/US2015/054084, dated Dec. 21, 2015.

Fernandez et al., "Adaptive and Mutational Resistance: Role of Porins and Efflux Pumps in Drug Resistance", Clinical Microbiology Reviews, Oct. 2012, vol. 25, No. 4, pp. 661-681.

Fornasiero et al., "Ion exclusion by sub-2-nm carbon nanotube pores", PNAS, Nov. 11, 2008, vol. 105, No. 45, pp. 17250-17255.

Liu et al., "Carbon Nanotube Based Artificial Water Channel Protein: Membrane Perturbation and Water Transportation", Nano Letters, 2009, vol. 9, No. 4, pp. 1386-1394.

Liu et al., "Ultrashort single-walled carbon nanotubes in a lipid bilayer as a new nanopore sensor", Nature Communications, Oct. 11, 2013, pp. 1-8.

Lopez et al., "Understanding nature's design for a nanosyringe", PNAS, Mar. 30, 2004, vol. 101, No. 13, pp. 4431-4434.

S. Wang et al., "Precise cutting of single-walled carbon nanotubes", Nanotechnology 18, Jan. 9, 2007, pp. 1-6.

Kushwaha et al., "Carbon nanotubes as a novel drug delivery system for anticancer therapy: a review", Brazilian Journal of Pharmaceutical Sciences, 2013, vol. 49, No. 4, 15 pages.

Nga No, "Virus-Like Membrane Fusion and Drug Delivery with Carbon Nanotube Porins", Lawrence Livermore National Laboratory, Dec. 19, 2019, 15 pages.

Chernomordik, L. V. & Kozlov, M. M., "Mechanics of membrane fusion", Natural Structural Molecular Biology, 15(7), Jul. 2008, pp. 675-683.

Epand, R. M., "Fusion peptides and the mechanism of viral fusion", Biochimica et Biophysica Acta, 1614,(2003, pp. 116-121.

Fornasiero, F. et al., "ph-tunable Ion Selectivity in Carbon Nanotube Pores", Langmuir (2010), 26(18), pp. 14848-14853.

Forterre, P., "The origin of viruses and their possible roles in major evolutionary transitions", Virus Research, 117 (2006), pp. 5-16.

Geng, J. et al., "Stochastic transport through carbon nanotubes in lipid bilayers and live cell membranes", Nature, vol. 514, Oct. 30, 2014, pp. 612-615.

Harrison, S. C., "Viral membrane fusion", Nature Structural & Molecular Biology, vol. 15, No. 7, Jul. 2008, 690-698.

Kneidl, B., Peller, M., Winter, G., Lindner, L. H. & Hossann, M., "Thermosensitive liposomal drug delivery systems: state of the art review", International Journal Nanomedicine, 9, 2014, pp. 4387-4398.

Buyukdagli, S. et al. Ionic Capillary Evaporation in Weakly Charged Nanopores. Phys. Rev. Lett. 105, 158103 (2010).

Dutt, M.J. et al. Interactions of End-functionalized Nanotubes with Lipid Vesicles: Spontaneous Insertion and Nanotube Self-Organization. Curr. Nanosci. 7, 699-715 (2011).

(56) References Cited

OTHER PUBLICATIONS

Stuurman, N. et al. Computer control of microscopes using µManager. Curr. Protoc. Malec. Biol., Chapter:14.20 (2010).
Fornasiero, F. et al. Ion Exclusion by sub 2-nm Carbon Nanotube Pores. Proc. Natl. Acad. Sci. USA 105, 17250-17255 (2008).
Frolov, V.A. et al. Shape bistability of a membrane neck: a toggle switch to control vesicle content release. Proc. Natl. Acad. Sci. 100, 8698-8703 (2003).
Gu, L.-Q. & Bayley, H. Interaction of the Noncovalent Molecular Adapter, β-Cyclodextrin, with the Staphylococcal α-Hemolysin Pore. Biophys. J 79, 1967-1975 (2000).
Hall, A.R. et al. Hybrid pore formation by directed insertion of α-haemolysin into solid-state nanopores. Nat. Nanotechnol. 5, 874-877 (2010).
Haque, F. et al. Incorporation of a viral DNA-packaging motor channel in lipid bilayers for real-time, single-molecule sensing of chemicals and double-stranded DNA. Nat. Protoc. 8, 373-392 (2013).
Hummer, G. et al. Water conduction through the hydrophobic channel of a carbon nanotube. Nature 414, 188-190 (2001).
Kam, N.W.S. et al. Carbon nanotubes as multifunctional biological transporters and near-infrared agents for selective cancer cell destruction. Proc. Natl. Acad. Sci. USA 102, 11600-11605 (2005).
Kasianowicz, J.J. et al. Characterization of individual polynucleotide molecules using a membrane channel. Proc. Natl. Acad. Sci. USA 93, 13770-13773 (1996).
Lacerda, L. et al. How do functionalized carbon nanotubes land on, bind to and pierce through model and plasma membranes. Nanoscale 5, 10242-10250 (2013).
Langecker, M. et al. Synthetic Lipid Membrane Channels Formed by Designed DNA Nanostructures. Science 338, 932-936 (2012).
Le Duc, Y. et al. Imidazole-Quartet Water and Proton Dipolar Channels. Angew. Chem. Int. Ed. SO, 11366-11372 (2011).
Lee, C.Y. et al. Coherence Resonance in a Single-Walled Carbon Nanotube Ion Channel. Science 329, 1320-1324 (2010).
Lev, A. et al. Rapid switching of ion current in narrow pores: implications for biological ion channels. Proc. Roy. Soc. B 252, 187-192 (1993).
Li, J. et al. Ion-beam sculpting at nanometre length scales. Nature 412, 166-169 (2001).
Liu, H. et al. Translocation of Single-Stranded DNA Through Single-Walled Carbon Nanotubes. Science 327, 64-67 (2010).
Neher, E. et al. Ionic selectivity, saturation, and block in gramicidin A channels. J Membr. Biol. 40, 97-116 (1978).
Nestorovich, E.M. et al. Residue ionization and ion transport through OmpF channels. Biophys. J 85, 3718-3729 (2003).
Powell, M.R. et al. Electric-field-induced wetting and dewetting in single hydrophobic nanopores. Nat. Nanotechnol. 6, 798-802 (2011).
Powell, M.R. et al. Nanoprecipitation-assisted ion current oscillations. Nat. Nanotechnol. 3, 51-57 (2007).
Shimizu, S. et al. Stochastic Pore Blocking and Gating in PDMS-Glass Nanopores from Vapor-Liquid Phase Transitions. J Phys. Chem. C 117, 9641-9651 (2013).
Shnyrova, A.V. et al. Geometric catalysis of membrane fission driven by flexible dynamin rings. Science 339, 1433-1436 (2013).
Sun, X. et al. Optical Properties of Ultrashort Semiconducting Single-Walled Carbon Nanotube Capsules Down to Sub-10 nm. J Am. Chem. Soc. 130, 6551-6555 (2008).
Venkatesan, B.M. & Bashir, R. Nanopore sensors for nucleic acid analysis. Nat. Nanotechnol. 6, 615-624 (2011).
Walther, J.H. et al. Barriers to Superfast Water Transport in Carbon Nanotube Membranes. Nano Lett. 13, 1910-1914 (2013).
Zimmerli, U. & Koumoutsakos, P. Simulations of Electrophoretic RNA Transport Through Transmembrane Carbon Nanotubes. Biophys. J 94, 2546-2557 (2008).
Yaroshchuk, A., "Non steric mechanisms of nano-filtration: superposition of Donnan and dielectric exclusion," Mar. 1, 2001, Sep. Purif. Technol., vol. 22-23, pp. 143-158.
Acharya, M. et al., (2000) "Transport in Nanoporous Carbon Membranes: Experiments and Analysis," AIChe J. 45(5): 911-922.

Ackerman, D.M. et al. (2003) "Diffusivities of Ar and Ne in Carbon Nanotubes," Molecular Simulation 29(10-11): 677-684.
Agre, P. et al. (2001) "Discovery of the Aquaporins and Their Impact on Basis and Clinical Physiology," Curr. Top. Membr. 51: 1-38.
Bass, R.B., et al., "Crystal Structure of *Escherichia coli* MscS, a Voltage-Modulated and Mechanosensitive Channel," Nov. 22, 2002, Nature, vol. 298, pp. 1582-1587.
Baudry, J. et al. (2001) "Experimental Evidence for a Large Slip Effect at a Nonwetting Fluid-Solid Interface," Langmuir 17: 5232-5236.
Beckstein, O., et al., "Not ions alone: barriers to ion permeation in nanopores and channels," Nov. 17, 2004, J Am Chem Soc., vol. 126, No. 45, pp. 14694-14695.
Beckstein, O., et al., "The influence of geometry, surface character and flexibility on the permeation of ions and water through biological pores" 2004, Phys. Biol., vol. 1, pp. 42-52.
Berezhkovskii, A., et al., "Single-File Transport of Water Molecules through a Carbon Nanotube," Jul. 23, 2002, Physical Review Letters, vol. 89, No. 6, 4 pages.
Bhatia, S.K., et al., "Comparisons of diffusive and viscous contributions to transport coefficients of light gases in single-walled carbon nanotubes," Aug. 2005, Molecular Simulation, vol. 31, No. 9, pp. 643-649.
Bird et al. (1960) "1.4 Theory of Viscosity of Gases at Low Density," Transport Phenomena Wiley, Ed. (New York), pp. 19-26.
Bittner, E.W. et al. (2003) "Characterization of the surfaces of single-walled carbon nanotubes using alcohols and hydrocarbons: a pulse adsorption technique," Carbon 41:1231-1239.
Carter, D.J., et al., "Incorporation of Cyano Transition Metal Complexes in KCI Crystals—Experimental and Computational Studies," 2003, Aust. J. Chem., vol. 56, pp. 675-678.
Cervera, J. et al. (2001) "Ion size effects on the current efficiency of narrow charged pores," J. Membrane Sci. 191:179-187.
Chen, H. et al. (2006) "Transport Diffusion of Gases is Rapid in Flexible Carbon Nanotubes," J. of Phys. Chem. B 110:1971-1975.
Chen, H. et al. (2006) "Predictions of selectivity and flux for CH4/H2 separations using single walled carbon nanotubes as membranes," J. Memb. Sci. 269:152-160.
Childress, A.E., et al., "Relating Nanofiltration Membrane Performance to Membrane Charge (Electrokinetic) Characteristics," 2000, Environ. Sci. Technol., vol. 34, No. 17, pp. 3710-3716.
Chopra, N., et al., "Bifunctional carbon nanotubes by side wall protection," May 2005 Adv. Funct. Mater. vol. 15, No. 5, pp. 858-864.
Cooper, S.M. et al. (2004) "Gas Transport Characteristics through a Carbon Nanotube," Nano Lett. 4(2):377-381.
Cottin-Bizonne, C. et al. (2002) "Nanorheology: An investigation of the boundary condition at hydrophobic and hydrophilic interfaces," Eur. Phys. J. E 9:47-53.
Craig, V.S.J. et al. (2001) "Shear-Dependent Boundary Slip in an Aqueous Newtonian Liquid," Phys. Rev. Let. 87(5):054504-1-054504-4.
Cui, H. et al. (2000) "Deposition of aligned bamboo-like carbon nanotubes via microwave plasma enhanced chemical vapor deposition," J. Appl. Phys. 88(10):6072-6074.
De Lint, W., et al., "Predictive charge-regulation transport model for nanofiltration from the theory of irreversible processes," 2004, J. Membrane Sci., vol. 243, pp. 365-377.
Dechadilok, P., et al., "Hindrance factors for diffusion and convection in pores," 2006, Ind. Eng. Chem. Res., vol. 45, pp. 6953-6959.
Deen, W.M., "Hindered transport of large molecules in liquid-filled pores," 1987, AICHE J, vol. 33, No. 9, pp. 1409-1425.
Donnan, F.G., "The Theory of Membrane Equilibria," 1924, Chem Rev, vol. 1, pp. 73-90.0.
Donnan, F.G., "Theory of membrane equilibria and membrane potentials in the presence of non-dialysing electrolytes. A contribution to physical-chemical physiology," Mar. 31, 1995, Journal of Membrane Science, vol. 100, No. 1. pp. 45-55. (Reprinted from Zeitshrift fur Electrochemie und Angewandte Physikalische Chemie, vol. 17, p. 572, 1911).

(56) References Cited

OTHER PUBLICATIONS

Doyle, D.A., et al., "The structure of the potassium channel: molecular basis of K conduction and selectivity," Science, 1998, vol. 280, No. 5360, pp. 69-77.

Elwenspoek et al. (1998) "14.4.5 Radical depletion in a trench," Silicon Micromachining, Cambridge Univ. Press: Cambridge, England:352-356.

Ganguli, S. et al. (1997) "Improved growth and thermal stability of Parylene films," J. Vac. Sci. Technol. A, 15(6):3138-3142.

Gao, H., et al., "Spontaneous Insertion of DNA Oligonucleotides into Carbon Nanotubes," 2003, Nano Letters, vol. 3, No. 4, pp. 471-473.

Harrell, C.C. et al. (2003) "Synthetic Single-Nanopore and Nanotube Membranes," Anal. Chem. 75:6861-6867.

Hata, K. et al. (2004) "Water-Assisted Highly Efficient Synthesis of Impurity-Free Single-Walled Carbon Nanotubes," Science 306:1362-1364.

Hinds, B.J., et al., "Aligned Multiwalled Carbon Nanotube Membranes," Jan. 2, 2004, Science, vol. 303, No. 5654, pp. 62-65.

Holt et al., "Fabrication of a Carbon Nanotube-Embedded Silicon Nitride Membrane for Studies of Nanometer-Scale Mass Transport", Nano Letters, vol. 4, No. 11 2004, pp. 2245-2250.

Holt, J.K., et al., "Fast Mass Transport Through Sub-2-Nanometer Carbon Nanotubes," May 19, 2006, Science, vol. 312, No. 5776, pp. 1034-1037.

Hou, H. et al. (2002) "Poly(p-xylylene) Nanotubes by Coating and Removal of Ultrathin Polymer Template Fibers," Macromolecules 35:2429-2431.

Hummer, G., "Water, proton, and ion transport: from nanotubes to proteins," Molecular Physics, 2007, vol. 105, Issue 2, pp. 201-207.

Hummer, G., et al., "Water conduction through the hydrophobic channel of a carbon nanotube," Nov. 8, 2001, Nature, vol. 414, No. 6860, pp. 188-190.

Lijima, S. et al. (1996) "Structural flexibility of carbon nanotubes," J. Chem. Phys. 104(5):2089-2092.

Itaya, K. et al. (1984) "Properties of Porous Anodic Aluminum Oxide Films as Membranes," J. Chem. Eng. Jpn. 17(5):514-520.

Jiang, Y., "Crystal structure and mechanism of a calcium-gated potassium channel," Nature. May 30, 2002, vol. 417, No. 6888, pp. 515-522.

Jiang, Y.X., et al., "The open pore conformation of potassium channels," May 30, 2002, Nature, vol. 417, pp. 523-526.

Joseph, S., et al., "Electrolytic Transport in Modified Carbon Nanotubes," 2003, Nano Letters, vol. 3, No. 10, pp. 1399-1403.

Kalra, A., et al., "Osmotic water transport through carbon nanotube membranes," Sep. 3, 2003, PNAS, vol. 100, No. 18, pp. 10175-10180.

Koga, K. "Formation of ordered ice nanotubes inside carbon nanotubes," Aug. 23, 2001, Nature, vol. 412, pp. 802-805.

Kolesnikov, A., et al., "Anomalously Soft Dynamics of Water in a Nanotube: A Revelation of Nanoscale Confinement," 2004, Phys. Rev. Lett., vol. 93, pp. 035503-1-035503-4.

Kotsalis, E.M. et al. (2004) "Multiphase water flow inside carbon nanotubes," Int. J. Multiphase Flow 30:995-1010.

Kronengold, J., et al., "Single-channel SCAM Identifies Pore-lining Residues in the First Extracellular Loop and First Transmembrane Domains of Cx46 Hemichannels," Oct. 2003, J Gen Physiol. vol. 122, No. 4, pp. 389013405.

Kumar, P. et al. (2008) "Polyethyleneimine-Modified MCM-48 Membranes: Effect of Water Vapor and Feed Concentration on N2/C02 Selectivity", Ind. Eng. Chem. Res. 47:201-208.

Kuo, A.L., et al., "Crystal Structure of the Potassium Channel KirBac1.1 in the Closed State Science," Jun. 20, 2003, vol. 300, No. 5627, pp. 1922-1926.

Lai, Z. et al. (2003) "Microstructural Optimization of a Zeolite Membrane for Organic Vapor Separation," Science 300:456-460.

Leger, C. et al. (1996) "Preparation and properties of surface modified ceramic membranes. Part III. Gas permeation of 5 nm alumina membranes modified by trichloro-octadecylsilane," J. Memb. Sci. (120):187-195.

Leung, K., et al., "Salt Permeation and Exclusion in Hydroxylated and Functionalized Silica Pores," Mar. 2006, Phys. Rev. Lett., vol. 96, No. 9, 4 pages.

Li, P.H., et al., "Tailoring wettability change on aligned and patterned carbon nanotube films for selective assembly," Feb. 22, 2007, J Phys Chem B. vol. 111, No. 7, pp. 1672-1678.

Lindsay, R.S. et al. (2003) "Test Results of Air-Permeable Charcoal Impregnated Suits to Challenge by Chemical and Biological Warfare Agents and Simulants: Summary Report", U.S. Amy Soldier and Biological Chemical Command Report, ECBC-TR, Aberdeen Proving Ground, MD, Unclassified Report.

Liu, H., et al., "Ion permeation dynamics in carbon nanotubes," 2003, J. Chem. Phys., vol. 125, 084713-1-084713-14.

Ma, R.Z. et al. (1998) "Processing and properties of carbon nanotubes-nano-SiC ceramic," J. Mater. Sci. 33:5243-5246.

Majumder, M., et al., "Effect of tip functionalization on transport through vertically oriented carbon nanotube membranes," Jun. 29, 2005, J Am Chem Soc. vol. 127, No. 25, pp. 9062-9070.

Majumder, M., et al., "Nanoscale hydrodynamics: Enhanced flow in carbon nanotubes," 2005, Nature, vol. 438, No. 7064, pp. 44.

Majumder, M., et al., "Voltage gated carbon nanotube membranes," Jul. 31, 2007, Langmuir, vol. 23, No. 16, pp. 8624-8631.

Melechko et al., "Vertically aligned carbon nanofibers and related structures: Controlled synthesis and directed assembly", Applied Physics Reviews, vol. 97, Feb. 3, 2005.

Miller, S.A., et al., "Electroosmotic Flow in Template-Prepared Carbon Nanotube Membranes," Dec. 12, 2001, J. Am. Chem. Soc., vol. 123, No. 49, pp. 12335-12342.

Miyazawa, A., et al., "Structure and gating mechanism of the acetylcholine receptor pore," Jun. 26, 2003, Nature, vol. 423, pp. 949-955.

Murakami, Y. et al. (2004) "Growth of vertically aligned single-walled carbon nanotube films on quartz substrates and their optical anisotropy," Chem. Phys. Lett. 385:298-303.

Murata, K., et al., "Structural determinants of water permeation through aquaporin-1," 2000, Nature, vol. 407, pp. 599-605.

Nagai, Y., et al., "Slow release of molecules in self assembling peptide nanofiber scaffold," Sep. 28, 2006, Journal of Controlled Release, vol. 115, No. 1, pp. 18-25.

Naguib, N. et al., (2004) "Observation of Water Confined in Nanometer Channels of Closed Carbon Nanotubes," Nano Lett. 4(11):2237-2243.

Nednoor, P., et al., "Carbon nanotube based biomimetic membranes: mimicking protein channels regulated by phosphorylation," 2007, J. Mater. Chem., vol. 17, pp. 1755-1757.

Nednoor, P., et al., Reversible Biochemical Switching of Ionic Transport through Aligned Carbon Nanotube Membranes,01D 2005, J. Chem. Mater., vol. 17, pp. 3595-3599.

Nightingale, E.R., Jr., "Phenomenological theory of ion solvation. Effective radii of hydrated ions," 1959, Journal of Physical Chemistry, vol. 63, No. 9, pp. 1381-1387.

Park, J.H., et al., "Ion separation using a Y-junction carbon nanotube," 2006, Nanotechnology, vol. 17, pp. 895-900.

Peter, C., et al., "Ion Transport through Membrane-Spanning Nanopores Studied by Molecular Dynamics Simulations and Continuum Electrostatics Calculations," Oct. 2005, vol. 89, No. 4, pp. 2222-2234.

Robertson, J.K. et al. (1994) "A Nested Electrostatically-Actuated Microvalve for an Integrated Microflow Controller," Proc. IEEE Micro Electro Mechanical Systems: 7-12.

Robertson, J.K. et al. (2001) "Modeling a microfluidic system using Knudsen's empirical equation for flow in the transition regime," J. Vac. Sci. Technol. A 19(1):358-364.

Roehl, J.E. et al. (2000) "Residual Life Indicators—Point Chemical Detectors Used to Measure the Capacity of Activated Carbon in Protective Garments, Gas Mask Filters, and Collective Protection Filters," Scentczar Corporation Report, Oct. 23-27:123-130.

Rogojevic, S. et al. (1999) "Modeling vapor deposition of low-K polymers: Parylene and polynaphthalene," J. Vac. Sci. Technol. 17(1):266-2743.

Rousseau, R., et al., "Modeling protonated water networks in bacteriorhodopsin," 2004, Phys. Chem. Chem. Phys. vol. 6, pp. 1848-1859.

(56) References Cited

OTHER PUBLICATIONS

Rutherford, S.W. et al. (1997) "Review of Time Lag Permeation Technique as a Method for Characterisation of Porous Media and Membranes," Adsorption 3:283-312.

Sakamoto, Y., et al., "Preparation and CO2 separation properties of amine-modified mesoporous silica membranes," Apr. 2007, Microporous and Mesoporous Materials, vol. 101, Issue 1-2, pp. 303-311.

Schaep, J., et al., "Influence of ionsize and charge in nanofiltration," Aug. 27, 1998, Separation and Purification Technology, vol. 14, No. 1-3, pp. 155-162.

Schaep, J., et al., "Modelling the retention of ioniccomponents for different nanofiltration membranes," Mar. 1, 2001, Separation and Purification Technology, vol. 22-23, pp. 169-179.

Skoulidas, A.I. et al. (2002) "Rapid Transport of Gases in Carbon Nanotubes," Phys. Rev. Lett. 89(18):185901-1-185901-4.

Sui H., et al., "Structural basis of water-specific transport through the AQP1 water channel," Dec. 20-27, 2001, Nature, vol. 414, No. 6866, ppl. 872-878.

Sumikama, T., et al., "Mechanism of ion permeation in a model channel: Free energy surface and dynamics of K plus ion transport in an anion-doped carbon nanotube, " Oct. 19, 2006, J Phys Chem B., vol. 110, No. 41, pp. 20671-20677.

Sun, L. et al. (2000) "Single Carbon Nanotube Membranes: A Well-Defined Model for Studying Mass Transport through Nanoporous Materials," J. Am. Chem. Soc. 122:12340-12345.

Tong, H.D. et al. (2004) "Silicon Nitride Nanosieve Membrane," Nano. Lett. 4(2):283-287.

Trexler, E.B., et al., "The first extracellular loop domain is a major determinant of charge selectivity in connexin46 channels," Dec. 2000, Biophys J., vol. 79, No. 6, pp. 3036-3051. Li.

Van Rijn, C. et al. (1997) "Deflection and Maximum Load of Microfiltration Membrane Sieves Made with Silicon Micromachining," J. Microelectromech. Sys. 6(1):48-54.

Van Rijn, C.J.M. et al. (1995) "Micro filtration Membrane Sieve with Silicon Micro Machining for Industrial and Biomedical Applications," IEEE Conf. MEMBS '95:83-87.

Vezenov, D.V., et al., "Force titrations and ionization state sensititve imaging of functional groups in aqueous solutions by chemical force microscopy," 1997, J. Am. Chem. Soc., vol. 119, pp. 2006-2015.

Weston, A, et. al. "Effect of electrolytecomposition on the separation of inorganic metal cations by capillary ion electrophoresis," Jun. 5, 1992, Journal of Chromatography A, vol. 602, Nos. 1-2, pp. 249-256.

Weston, A., et. al., "Factors affecting the separation of inorganic metal cations by capillary ectrophoresis," Feb. 28, 1992, Journal of Chromatography A, vol. 593, Nos. 1-2, pp. 289-295.

Wikstrom M.,"Water-gated mechanism of proton translocation by cytochrome c oxidase," Biochim Biophys Acta., Jun. 5, 2003, vol. 1604, No. 2, pp. 61-65.

Wikstrom, M., "Proton translocation by bacteriorhodopsin and heme-copper oxidases," Aug. 1998, Curr Opin Struct Biol., vol. 8, No. 4, pp. 480-488.

Williams, M.E. et al. (1999) "Separation of Organic Pollutants by Reverse Osmosis and Nanofiltration Membranes: Mathematical Models and Experimental Verification," Ind. Eng. Chem. Res. 38(10):3683-3695.

Wong, S.S., et al., "Covalently Functionalized Nanotubes as Nanometer-Sized Probes in Chemistry and Biology," Jul. 2, 1988, Nature, vol. 394, pp. 52-55.

Wong, S.S., et al., "Covalently-Functionalized Single-Walled Carbon Nanotube Probe Tips for Chemical Force Microscopy," 1998, J. Am. Chem. Soc., vol. 120, pp. 8557-8558.

Yang, D.Q., et al., "Controlled chemical functionalization of multiwalled carbon nanotubes by kiloelectronvolt argon ion treatment and air exposure," Aug. 30, 2005, Langmuir, vol. 21, No. 18, pp. 8539-8545.

Yu, M. et al. (2005) "Interphase exchange coupling in Fe/Sm—Co bilayers with gradient Fe thickness," J. Appl. Phys. 98:063908-1-06908-4.

Zhu, J. et al. (2002) "Density-Induced Interchange of Anisotropy Axes at Half-Filled High Landau Levels," Phys. Rev. Lett. 88(11):116803-1-116803-4.

Li, J. et al. (1999) "Highly-ordered carbon nanotube arrays for electronics applications," Appl. Phys Lett. 75(3):367-369.

* cited by examiner

SEQUENCE LISTING

```
<160> NUMBER OF SEQ ID NOS: 1

<210> SEQ ID NO 1
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcggccgcta ctagtcttac cgccacccag agggccataa cgggtacggt attggcttac        60
acggttacgc agacgctgta c                                                  81
```

NANOTUBE TRANS-MEMBRANE CHANNELS MIMICKING BIOLOGICAL PORINS

CROSS-REFERENCE TO RELATED APPLICATION

This application is a national phase application under 35 U.S.C. § 371 of International Application No. PCT/US2015/054084, filed Oct. 5, 2015, which in turn claims priority under 35 U.S.C. § 119(e) to U.S. Provisional Application No. 62/060,494, filed Oct. 6, 2014, the content of each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 1, 2017, is named 093866-7061_SL.txt and is 778 bytes in size.

BACKGROUND

Living systems control the transport of ions or small molecules across biological membranes to maintain non-equilibrium concentration gradients and to transmit chemical signals. To carry out these tasks, biological organisms have developed a sophisticated arsenal of membrane channels that form highly-efficient and selective pores in lipid bilayers. Although bottom-up synthesis and top-down fabrication could produce pores of comparable size, an unresolved challenge remains to build nanopore scaffolds that fully replicate the transport properties of membrane channels.

Existing examples of nanopores may be characterized as falling into three categories: synthetic ion channels made by bottom-up synthesis and providing a mimic of the trans-membrane pore, solid-state nanopores, usually drilled or etched out of solid pieces of material matrix, and biological nanopores made by isolating a naturally-occurring protein.

SUMMARY

The present invention is directed to nanopore structures, nanoporous membranes, methods of synthesis, and various methods of using said nanoporous structures, and which exhibit the features of those three existing types of pores while substantially mitigating a number of shortcomings exhibited by each of these types of pores.

Aspects of the present invention include:
(i) a method to produce, (and the nanotubes prepared by these methods), and to synthesize a nanopore structure or structures having an ultra-short nanotube, with length of about 1 nm to 100 nm and coated with an amphiphilic coating. In one aspect, the method comprises segmenting (e.g. via sonication) the nanotube(s) in the presence of an amphiphilic material, including but not limited to 1,2-dioleoyl-sn-glycero-3-phosphocholine (DOPC) or 1,2-diphytanoyl-sn-glycero-3-phosphocholine (DPhPC), or phospholipids, or block co-polymers. One advantage of this nanopore structure prepared by this method is the extended stability at room and/or elevated temperature. This method can be used to produce other short nanotubes beside those made of carbon, boron nitride, and $MoS_2$;
(ii) A nanopore structure that comprises a short nanotube(s), incorporated in a membrane comprised of lipid molecules that can be used for the spontaneous or forced incorporation of nanotubes into a lipid membrane, for example a planar lipid bilayer, liposome vesicles; and also incorporation into cell membrane. This activity mimics the functionality of biological membrane proteins, including enabling the ion and molecule transport from one side of the membrane to another. In one aspect, the membrane comprises a plurality of nanotubes, that in one aspect are substantially perpendicular to the plane of the membrane;
(iii) This nanopore structure (which may also be characterized as a "porin-like structure" or in one aspect a "carbon nanotube porin" or CNP structure) can be used to deliver therapeutic, imaging, transfection and other agents into human or mammalian cells for various purposes. The agents can be either incorporated inside the vesicles, or conjugated to the nanotubes, or the combination of both;
(iv) The NTs can be used as therapeutic or an antimicrobial agents to inhibit the growth of or kill microorganisms and lyse cell membranes and treat disease associated with the presence of the microorganism in a subject, such as a human patient, or in or on a surface;
(v) The NT opening can be modulated by transmembrane chemical gating, and covalently attached "gatekeeper" moieties;
(vi) NTs can be used for biosensing applications taking advantage of exceptional chemical and biological stability of NTs. It can also be integrated into bioelectronics devices or lab-on-a-chip architectures; and
(vii) NTs can be used as a synthetic nanopore for direct readout single-chain sequencing of DNA and other polymer chains.

Details regarding the above aspects are provided in the Detailed Description provided herein.

BRIEF DESCRIPTION OF THE FIGURES

FIG. 13A. Schematic of the on-cell patch clamp measurement. B, C. On-cell conductance measurements demonstrate no channel activity (A) and appearance of a small flickering channel (B) in control experiments with HEK293T cells. Holding potentials were −60 mV (A) and +60 mV (B), the time order is from left to right, up to bottom. D. In presence of CNT porin (0.15% dilution of the stock), large channel activity is detected, holding potential −60 mV. E. Metastable conductance sub-states of 50 pS detected with CNT porin incorporated into the plasma membrane of CHO cell, holding potential was −60 mV. F. Mean patch conductance (on cell configuration, 0.15% CNT stock solution in the patch pipette) detected in CHO and HEK293T cells at positive and negative holding potentials. Error bar: s.d., 4 cells). In ~70% of HEK293T cells and 95% of CHO cells. Applicants did not observe significant dependence of the conductance on the holding potential; only those cells were used for the conductance analysis.

DETAILED DESCRIPTION

Definitions

Figure 1:
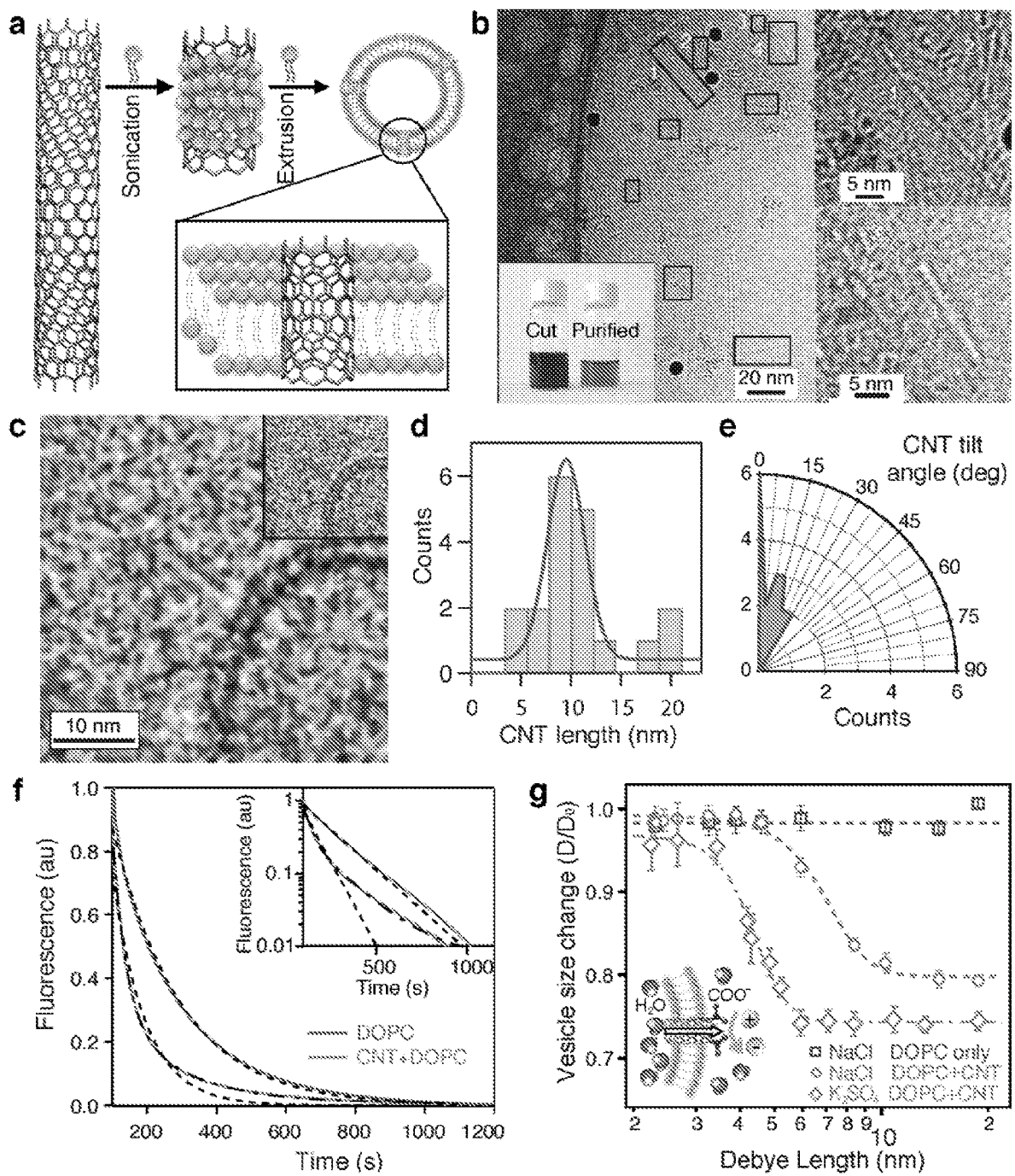
FIGS. 1A-1G: Synthesis, characterization, and bulk transport properties of CNT porins. A. Schematic showing CNT porin preparation and incorporation into liposomes. B. TEM image of cut CNTs stabilized by lipid coating. Panels on the right show magnified regions of the TEM image. Inset: a photograph of cut CNT suspensions before and after centrifugation. C. Cryo-TEM image of a CNT porin. Inset: overlaid outlines of the bilayer (dark grey) and CNT (light grey, straight line). Image was processed to enhance contrast (see FIGS. 5A-5M for unfiltered images of this and other CNT porins). D. Histogram of the lengths of the CNTs inserted into the lipid membrane and a Gaussian fit to the data. (n=20). E. Radius plot of the histogram of CNT tilt angles measured relative to the axis normal to the bilayer plane. (n=20). F. Time traces of the fluorescence of HPTS dye encapsulated in liposomes with and without CNT porins after outside pH was lowered from pH=8 to pH=3. Dashed lines: single exponential fits; dash-dotted line: a sum of two exponential terms. G. Plot of the liposome size change after exposure to NaCl (circles and squares) and $K_2SO_4$ (diamonds) osmotic gradients. Dashed lines: fits to sigmoidal function. Error bars, s.d. (n=4-5).

Before the present compositions, and methods are described, it is to be understood that the invention is not limited to the particular methodologies, protocols, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Throughout and within this disclosure, patent and technical literature are referenced by an identifying citation or an Arabic number within parentheses, the full citations of which are found in the section immediately preceding the claims. All technical and patent publications cited herein are incorporated herein by reference in their entirety. Nothing herein is to be construed as an admission that the invention is not entitled to antedate such disclosure by virtue of prior invention.

In accordance with the present invention and as used herein, the following terms are defined with the following meanings, unless explicitly stated otherwise.

As used in the specification and claims, the singular form "a", "an" and "the" include plural references unless the context clearly dictates otherwise.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about". It also is to be understood, although not always explicitly stated, that the reagents described herein are merely exemplary and that equivalents of such are known in the art.

As used herein, the term "comprising" or "comprises" is intended to mean that the devices and methods include the recited elements, but not excluding others. "Consisting essentially of" when used to define devices, methods, or kit of parts, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace amount of elements of other ingredients and substantial method steps. Embodiments defined by each of these transition terms are within the scope of this invention.

As used herein, the term "substantially perpendicular" intends less than about 25 degrees, or alternatively less than about 20 degrees, or alternatively less than about 15 degrees, or alternatively less than about 10 degrees, from a 90 degree angle from the reference plane, e.g. less than about 75 degrees, or alternatively less than 80 degrees, or alternatively less than 85 degrees from the reference plane.

As used herein, the term "substantially the same length" intends less than a 5%, or alternatively less than about 4%, or alternatively less than 3%, or alternatively less than 2%, or alternatively less than about 1%, difference from the reference length.

As used herein, the term "liquid" refers to any liquid that has the particles loose and can freely form a distinct surface at the boundaries of its bulk material. Examples of liquid include, but are not limited to, water, industrial streams, chemicals, or bodily liquids. Examples of water include, without limitation, salted water, sea water, well water, underground water, and waste water. Examples of industrial stream include, without limitation, pharmaceutical industry process stream, or food industry process stream. Examples of chemicals include, without limitation, chemicals used in pharmaceutical industry, laboratories, or research organizations. Examples of bodily liquids include, without limitation, diluted, untreated, or treated body fluids such as milk, blood, plasma, urine, amniotic liquid, sweat, saliva, etc.

As used herein, the term "membrane" intends a porous material whose lateral dimension is significantly larger than the dimensions across it.

As used herein the term "nanotube" intends a substantially cylindrical tubular structure of which the most inner diameter size is an average of about nm to about 10 nm, and ranges in between.

Nanotubes are comprised of various materials, which include but are not limited to carbon, silicon, $MoS_2$, silica and selenium. Inorganic nanotubes such as boron nitride have also been synthesized. Carbon nanotubes include single wall, double wall, and multiwall types. A "single-wall" is one tubular layer, straight or tortuous, of carbon atoms with or without a cap at the ends, while a "double-wall" is two concentric tubular layers, straight or tortuous, of carbon atoms with or without a cap at the ends and a "multi-wall" intends more than two concentric tubular layers, straight or tortuous, of carbon atoms with or without a cap at the ends. Nanotubes having the appropriate internal diameter can be purchased from commercial sources or synthesized using techniques known in the art.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown A "composition" is intended to mean a combination of a NT or a membrane containing an NT, and another compound or composition, inert (for example, a detectable agent, dye or label or an acceptable carrier) or active, such as an antimicrobial or other therapeutic agent.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

An "effective amount" is an amount sufficient to effect beneficial or desired results. An effective amount can be administered in one or more administrations, applications or dosages as determined by the treating physician or professional.

An amphiphilic membrane or coating intends a polymer or large molecule having an hydrophobic end and a hydrophilic end. In one aspect the amphiphilic membrane or coating is capable of a liposome, include for example, phospholipids, such as hydrogenated soy phosphatidylcholine (HSPC), lecithin, phosphatidylethanolamine, lysolecithin, lysophosphatidylethanolamine, phosphatidylserine, phosphatidylinositol, sphingomyelin, cephalin, cardiolipin, phosphatidic acid, cerebro sides, distearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioleoylphosphatidylglycerol and (DOPG), dicetylphosphate that are able to form vesicles.

A "subject," "individual" or "patient" is used interchangeably herein, and refers to a vertebrate, preferably a mammal, more preferably a human. Mammals include, but are not limited to, murines, rats, rabbit, simians, bovines, ovine, porcine, canines, feline, farm animals, sport animals, pets, equine, and primate, particularly human. Besides being useful for human treatment, the present disclosure is also useful for veterinary treatment of companion mammals, exotic animals and domesticated animals, including mammals, rodents, and the like.

Modes for Carrying Out the Disclosure

Nanopore Compositions

In one aspect, the present disclosure provides nanopore structure comprising a nanotube(s), or alternatively consisting essentially of, or yet further consisting of, (NTs) coated with an amphiphilic material and having length of from about 1 nm to about 100 nm, or alternatively from about 1 to about 50 nm, or alternatively from about 1 nm to about 30 nm, or alternatively from about 1 nm to about 15 nm, or alternatively from about 1 nm to about 12 nm, or alternatively from about 1 nm to about 5 nm, or alternatively less than 100 nm, or alternatively less than about 50 nm, or alternatively less than about 30 nm, or alternatively less than about 15 nm, or alternatively less than 10 nm, or alternatively from about 2 nm to about 30 nm, or alternatively from about 2 nm to about 15 nm, or alternatively from about 3 nm to about 15 nm.

In one aspect the nanotubes have an internal diameter of 0.5 Angstroms to about 15 nm, or alternatively from about 0.5 nm to about 15 nm, or alternatively from about 0.5 nm to about 10 nm, or alternatively from about 1 nm to about 15 nm nanometers, or an average diameter of less than about 20 nm, or alternatively less than about 15 nm, or alternatively less than about 10 nm, or alternatively less than about 5 nm, or alternatively less than about 2 nm, or alternatively less than about 1 nm.

The nanotubes can be made of a variety of materials, non-limiting examples of such include carbon nanotube, boron nitride, and molybdenum disulfide.

In a further aspect, the NT has a length of from about 3 nm to about 15 nm in length and has an internal diameter of from about 0.5 nm to about 15 nm.

Any appropriate amphiphilic material can be coated onto the NT and non-limiting examples of such include without limitation a phospholipid, a block-copolymer, 1,2-dioleoyl-sn-glycero-3-phosphocholine (DOPC), and 1,2-diphytanoyl-sn-glycero-3-phosphocholine (DPhPC). In one aspect, the amphiphilic coating is capable of facilitating self-insertion of the nanotube(s) through a membrane, as described below.

Similar to the NTs, these materials are commercially available or can be synthesized using known laboratory techniques.

The NTs can be further functionalized by the addition to one or both ends of a molecule such as a dendrimer or a polynucleotide, or, alternatively, by the addition of a charge. The additional group can be covalently attached to the one or both ends of the NT(s). Methods to functionalize NTs are known in the art and described in US Patent Appl. Publ. No. 2012/0261620 and U.S. Pat. Nos. 8,541,322 and 7,572,426.

This disclosure also provides amphiphilic membranes having one or more of the amphiphilic coated NT(s) incorporated into an amphiphilic membrane. In one aspect, wherein a plurality of the NTs are incorporated in a membrane, the plurality can be the same or different NT material (e.g., carbon NTs and $MoS_2$ NTs), and coated with the same or same or different amphiphilic material. In addition, the NTs can have the same or different internal diameters and the same or different length. In a yet a further aspect, the NTs can be similarly or differently functionalized. In a further aspect, the NT is substantially equal to, or greater than (i.e., longer) than the thickness of the amphiphilic membrane. In a further aspect, the NT is longer than the amphiphilic membrane thickness.

In one aspect, the amphiphilic membrane can be the same, of similar composition (e.g., both a block copolymer or both a phospholipid) or different from the amphiphilic coating on the NTs. In one aspect, the coating and membrane are identical.

In aspect, the membrane is an amphiphilic membrane that forms a vesicle in solution, e.g., a liposome, a planar lipid bilayer or a micelle.

In a further aspect, when the one or more NT is incorporated into the membrane, one or more of the NTs are substantially perpendicular to the plane of the membrane. In one aspect, at least one of the NTs are incorporated into the membrane, at least 50%, or alternatively at least 60%, or alternatively at least 70%, or alternatively at least 80%, or alternatively at least 85%, or alternatively at least 90%, or at least 95%, or alternatively at least 97%, substantially perpendicular In one aspect, the membrane is a lipid that forms a vesicle or liposome or micelle and the vesicle further comprises a cargo moiety, where non-limited examples of such cargo moiety include, without limitation, a small molecule, drug, an imaging agent, or a polynucleotide.

In one aspect, the nanopore structures comprise ultra-short carbon nanotubes (CNTs) coated with an amphiphilic material, which spontaneously self-insert into a lipid membrane and form channels with transport properties that are remarkably similar to those of the biological porin proteins. These CNT porins can transport chemical species, e.g., compounds, molecules, drugs, liquids such as water, protons, and small ions. In one aspect, the CNT pores further comprise a charge at the end of the CNT, and their ion-rejection properties can be controlled by the charge at the pore entrance. In another aspect, the CNTs further comprise single-stranded polynucleotides attached to at least one termini, such as ssDNA that provides electrophoretically-driven translocation of individual single-stranded DNA molecules through the CNT porins that produces well-defined ion current blockades even at low bias voltages. Overall, CNT porins represent a robust and versatile biomimetic scaffold for studying fundamentals of transport in biological channels, artificial cell design, and stochastic sensing.

This disclosure also provides compositions comprising one or both of the NTs and membranes embedded with NTs in a carrier, e.g., a carrier to assist with diagnostic, research or therapeutic use as noted herein. The compositions can be further processed, for example, by lyophilisation for stability and portability.

Preparation Methods

This disclosure also provides a method to prepare a nanopore structure as described above, the method comprising, or alternatively consisting essentially of, or yet further consisting of, segmenting a nanotube into shorter segments in the presence of an effective amount of amphiphilic material in a solvent in for example, water, saline or other appropriate solvent and under conditions so that the segmented nanotubes are coated by the amphiphilic material and segmented. In one aspect, the effective amount comprises ratios of 60 (amphiphilic):1 (NT), about about 30:1, or alteratively 25:1, or alternatively 20:1, or alternatively 15:1, or alternatively 10:1, or alternatively 5:1, or alternatively 2:1. In one aspect, the NT is segmented by ultrasonication performed and for a time to segment the NTs, which can be empirically determined using methods described herein. In one aspect, the amphiphilic material is of a type capable of facilitating self-insertion of the nanotube(s) through an amphiphilic membrane to form a transmembrane pore(s).

After sonication, larger uncut NTs can be removed from the mixture, which can be accomplished by any appropriate method, e.g., by centrifugation or filtration.

This disclosure also provides a method to make an amphiphilic membrane permeable, comprising, or alternatively consisting essentially of, or yet further consisting of introducing a nanopore structure(s) comprising one or more nanotube(s) coated with an amphiphilic material to the amphiphilic membrane, so that the nanopore structure(s) self-inserts through the amphiphilic membrane to form a transmembrane pore(s). The membranes can be any appropriate thickness, as described above, e.g., 5 nm and in one aspect, is about or just less than the length of the NTs.

In one aspect the membrane is one that self-assembles into a microvesicle, non-limiting examples of such include phospholipids such as DOPC.

In one aspect, an effective amount of a cargo moiety is added to the amphiphilic coated NTs and the amphiphilic membrane, to incorporate the cargo moiety into the lumen of the vesicle. In one aspect, the vesicle is prepared by extrusion or other mechanical technique in the presence of the internal cargo. The encapsulated cargo is separated from the free cargo by any appropriate method, e.g., by use of a size exclusion chromatography. The coated NTs can be added before, during, or after preparation of the vesicles.

In accordance with the above methods, and using CNT as an example, a CNT porin preparation procedure involves, but is not limited to, the following. Approximately 2 mL of DOPC (10 mg/mL in chloroform) was added to about 20 mL glass vial and the solvent was evaporated to form a thin lipid film on the walls of the glass vial. 1.6 mg of purified CNTs and 20 mL deionized water (DI) water were then added to the same vial. The mixture was first bath-sonicated for 1 hr, and then probe-sonicated for 16 hrs at 100 W power. The sonicator was set to run in 3-second pulses with a 1-second pause between each pulse. During sonication, the vial was continuously cooled in an ice-water bath. If necessary, deionized water was added to the vial periodically during sonication to compensate for any loss in sample volume due to evaporation. To separate the cut CNTs from the uncut nanotube material, 10 mL of suspension processed by sonication cutting was added to a 15 mL centrifuge tube and centrifuged at 4000 rpm for 1 hr. After centrifugation, Applicants extracted the supernatant containing purified CNT/DOPC complex.

Figure 5:
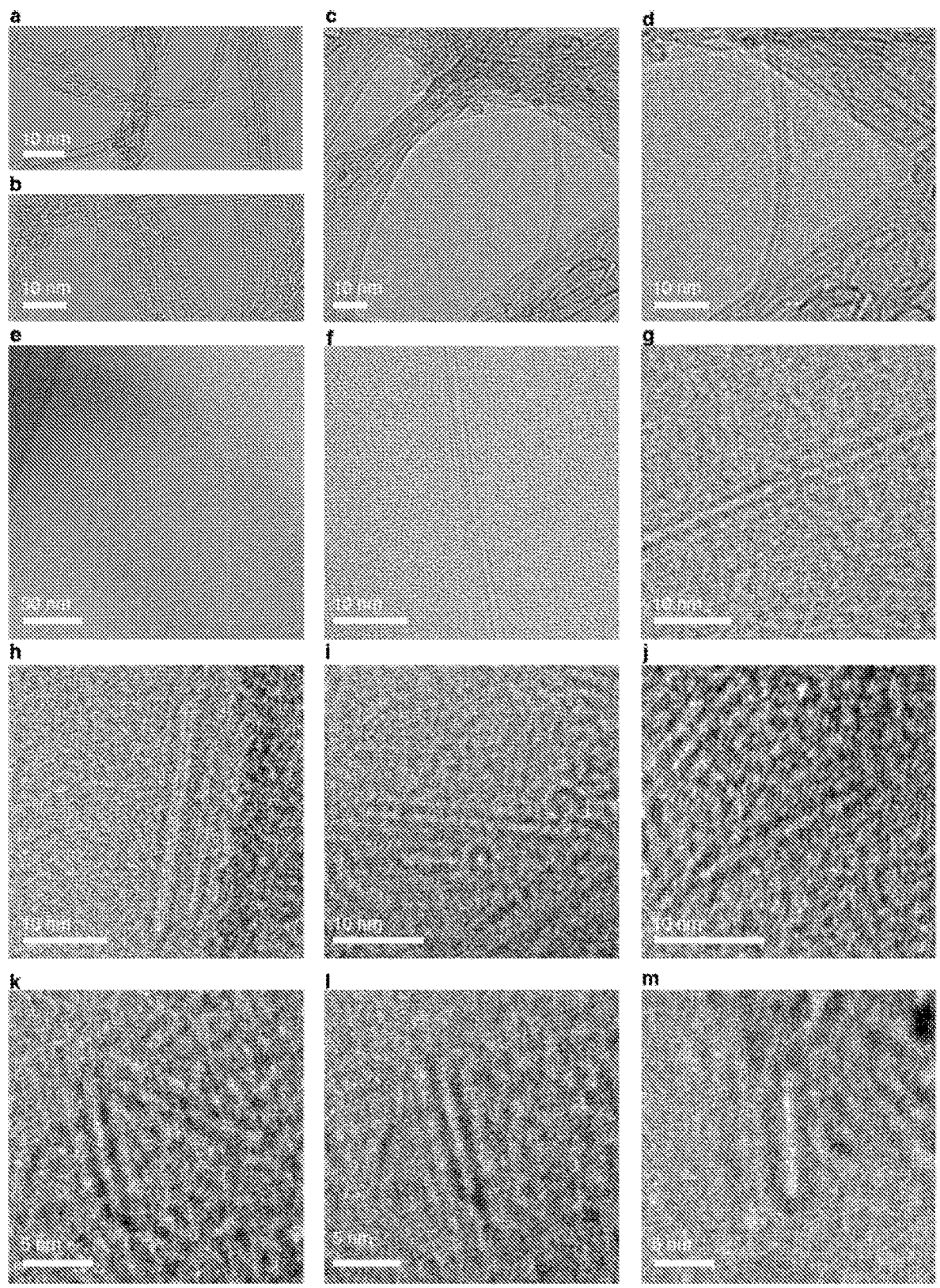
FIGS. 5A-5M: TEM images of isolated CNTs. A-C. Purified CNTs before cutting (A, B conventional TEM, C imaged on a cryo stage; all air-dried samples). D. Magnified image of one CNT from (C). E-G. CNTs mixed with lipid and lightly sonicated to aid nanotube dispersion. H-M. Isolated CNT porins after the cutting procedure.
Figure 6:
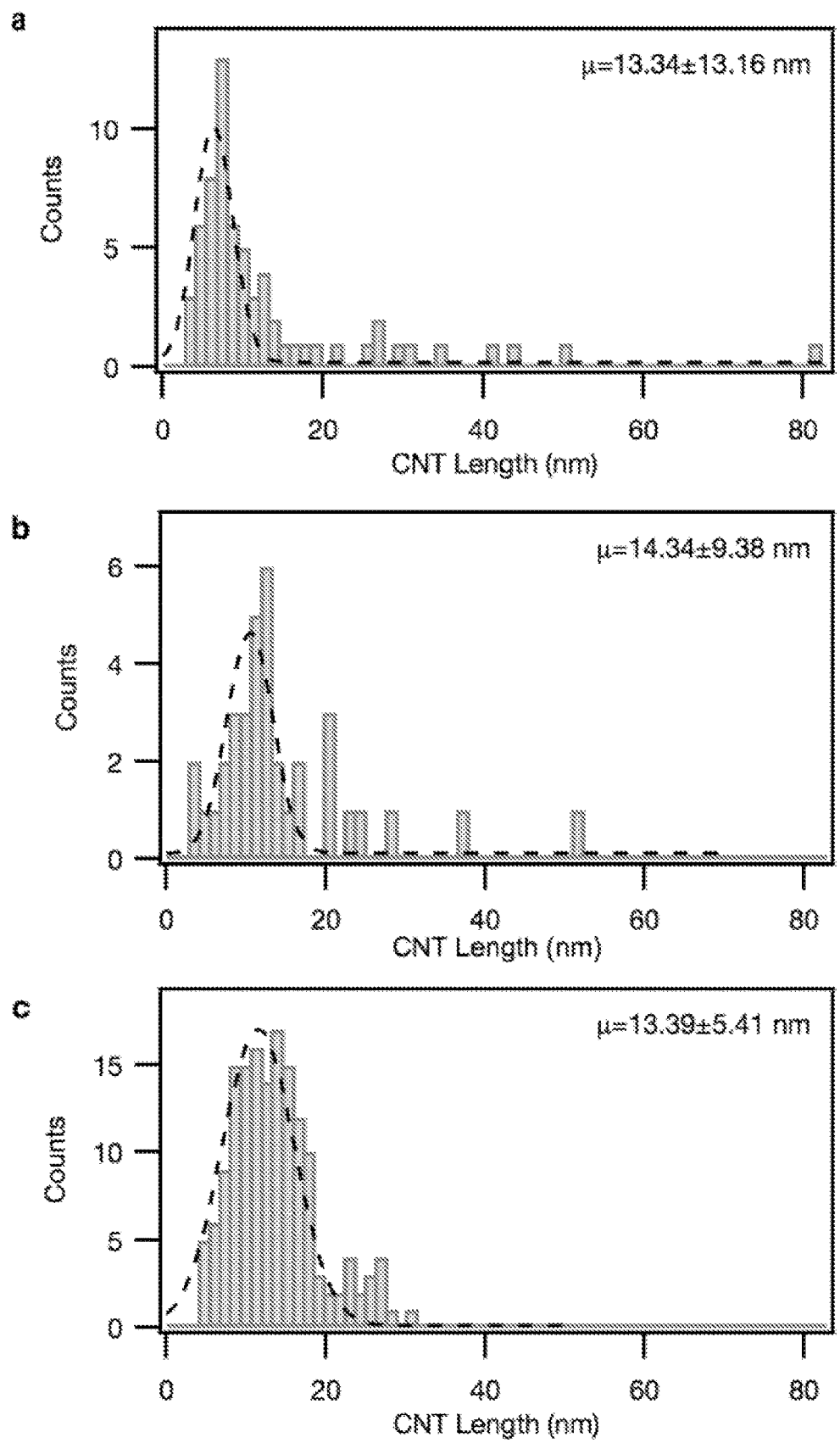
FIGS. 6A-6C: Length distributions of CNT porins measured from TEM images. A. CNT porin sample after cutting and purification procedures. (n=65). B. Cut and purified sample after passing through a 100 nm pore filter membrane. (n=36). C. Cut and purified sample after passing through a 50 nm pore filter membrane. (n=156).

In accordance with the methods described above, carbon NTs (CNTs) were prepare by sonication-induced cutting of purified 1.51±0.21 nm average inner diameter CNTs (see Materials and Methods below for details on the procedure, transmission electron microscopy (TEM) images of uncut CNTs (FIGS. 5A-5M), atomic force microscopy (AFM) analysis of CNT diameters (FIGS. 6A-6C), and additional CNT characterization) was conducted followed by separation of longer uncut fragments by centrifugation, produced a stable dark suspension that contained short CNTs stabilized by the lipid coating (FIG. 5B, inset). Therefore, this disclosure also provides the CNT porins produced by these methods.

Applicants were able to repeatedly dry the sample and re-suspend it in water, indicating that the lipid coating protected the cut CNTs from forming large aggregates. Raman spectroscopy confirmed that the cutting procedure preserved the inner diameter and rolled-up graphene sheet structure of the nanotube remarkably well (see FIGS. 6A-6C). High-resolution TEM images of the purified short CNT fragments (FIG. 4B) indicate that the purified product contains a significant population of CNT fragments in the ca. 10 nm range (the average length of the nanotube fragments determined from the TEM images was 10.1±5.4 nm).

After reconstituting purified short CNT fragments into 200 nm diameter lipid vesicles (see Materials and Methods, for the extrusion protocol), the resulting vesicles were imaged using cryogenic transmission electron microscopy (cryo TEM). The images of the vesicles revealed clear evidence of short CNT fragments inserted into the lipid membrane and spanning both of the membrane leaflets (FIGS. 1C-1F). Cryo TEM images also show that the presence of CNT porins does not affect the integrity of the lipid bilayer.

Statistical analysis of cryo TEM data reveals several interesting features of the CNT porins. First, the average length of the CNTs inserted into the membrane, 9.5±3.0 nm, was in excellent agreement with the 10.1 nm average length of the cut CNTs, indicating that the insertion procedure was not selective to any particular length. Second, CNT porins did not insert into the membrane at random angles. The histogram of the measured tilt angles (FIG. 1G) shows that the nanotubes strongly prefer the perpendicular orientation to the membrane plane with the majority of the nanotube tilting only by 15 degrees or less. This observation is somewhat surprising, since MD simulations had predicted that CNTs longer than the thickness of the bilayer (4.6±0.2 nm for the 1,2-dioleoyl-sn-glycero-3-phosphocholine (DOPC) that were used in the Materials and Methods), should tilt to maximize the interactions of the hydrophobic bilayer core with the hydrophobic CNT walls (11). It is possible that the lipid coating remaining on the walls from the cutting procedure provided additional stabilization to the portion of the CNT that protruded from the bilayer. Higher contrast (e.g., FIG. 1E) on the protruding portion of the CNT porins that were sometimes observed in the cryo TEM images supports this possibility. Third, CNT porins were always inserted in such a way that at least one end of the channel abutted the hydrophilic head groups of the lipid bilayer. Unlike the situation when both of the CNT porin ends protrude into the solution, this configuration does allow for the energetically favorable interactions of the hydrophilic groups on one of the CNT ends with the hydrophilic headgroups of the lipid bilayer.

To incorporate CNTs into DOPC vesicles, a 0.2 mL aliquot of 10 mg/mL DOPC in chloroform was added to a 20 mL glass vial and the solvent was evaporated to leave a dried lipid film. 1 mL of purified CNT/DOPC complex solution was added to the vial and the mixture was allowed to hydrate for one hour. The solution was then extruded through a 200 nm-diameter pore polycarbonate membrane using a hand-held extrusion device for 10 cycles to produce a solution that contained the lipid vesicles with carbon nanotube pores.

The CNT porins enable efficient transport of chemical species across the lipid bilayer. For initial assessment of the porin properties, Applicants investigated proton transport into vesicle lumens containing an encapsulated pH-sensitive dye (8-hydroxypyrene-1,3,6-trisulfonic acid trisodium salt (HPTS)). For these experiments, the vesicles were prepared with a lumen pH of 8.1 and subsequently transferred them into a solution of pH of 3.0 to create a proton gradient across the vesicle membrane. All solutions also contained a high concentration of background KCl electrolyte to ensure the absence of an osmotic pressure gradient across the lipid bilayer. The decay of the HPTS fluorescence, FIG. 1D indicated that once the proton gradient was established, the protons were transported into the vesicle lumen space. In the absence of the CNT channels, the fluorescence decay followed single-exponential kinetics with a characteristic time of 187 s, clearly indicating the existence of a single pathway for protons to enter the vesicle lumen by diffusing through the lipid bilayer. After the CNT porins were inserted into the vesicle walls, no leakage of the HPTS dye from the vesicles was observed indicating that the CNT pores were impermeable to the HPTS. However, the proton transport experiments with these vesicles produced much faster fluorescence decay (FIG. 1D). Significantly, the decay kinetics no longer followed a single-exponent form, but instead represented a sum of two exponential terms, with the first term matching the 187 s timescale obtained in a control experiment, and the second term having a much faster characteristic time of 35 s (FIG. 1D, inset). This result confirms that the addition of CNT pores to the vesicle wall formed a second pathway for protons to enter the vesicle inner space.

Applications and Methods

The coated NTs and membranes have diagnostic and therapeutic utilities. In one aspect, this disclosure provides method of drug delivery, comprising introducing a nanopore structure(s) comprising a NT coated with an amphiphilic material to an amphiphilic membrane, so that the nanopore structure(s) self-inserts through the amphiphilic membrane to form a transmembrane pore(s); and delivering a drug through the amphiphilic membrane via the transmembrane pore(s) formed by the nanopore structure(s).

Also provide herein is a method of delivering an imaging agent delivery to a cell, or a collection of cells, or a tissue, comprising introducing a nanopore structure(s) comprising a nanotube(s) coated with an amphiphilic material to a cell membrane, so that the nanopore structure(s) self-inserts through the cell membrane to form a transmembrane pore(s); and delivering an imaging agent through the cell membrane into the cell interior via the transmembrane pore(s) formed by the nanopore structure(s). Other cargo, e.g., a therapeutic agent, can be similarly delivered.

Also provided is a method of sequencing nucleic acids, comprising introducing a nanopore structure(s) comprising a nanotube(s) coated with an amphiphilic material to an amphiphilic membrane, so that the nanopore structure(s) self-inserts through the amphiphilic membrane to form a transmembrane pore(s); providing a voltage across the nanopore structure(s) to induce a measurable current flow there through; translating nucleic acid polymer through the transmembrane pore(s) using electrophoretic force or other means; and measuring the ion current through the transmembrane pore(s) over time to assist in determining DNA sequence.

This disclosure also provides a method of eliminating or inhibiting the growth of undesirable microorganisms in an environment amenable to their growth, comprising adding nanopore structure(s) comprising a carbon nanotube(s) coated with an amphiphilic material to the environment in an amount sufficient to eliminate or inhibit such microbial growth. In one aspect, the coated NTs are co-administered with an effective amount of an drug or therapeutic that will inhibit or kill the microorganism (e.g., bacteria or virus) or the drug or agent is encapsulated within a vesicle containing the coated NTs. The agent can be delivered or administered before, simultaneously, or after the coated NTs.

Yet further provided is a method for delivering a therapeutic agent, drug or other agent to patient comprising administering an effective amount of the vesicle containing the therapeutic agent, drug or other agent to the subject in need of the therapeutic agent, drug or other agent. In one aspect, the composition can be used to treat a microbial infection in a subject in need thereof, when the vesicle comprises an antibiotic that will inhibit the growth of, or kill the microbe causing the infection.

The following examples are provided to illustrate, not limit the disclosure

Materials and Methods

Materials.

1.5 nm diameter single-walled carbon nanotubes were purchased from NanoLab Inc. (Waltham, Mass., USA, product purity >95%). 1, 2-dioleoyl-sn-glycerol-3-phosphocholine (DOPC), 1,2-dioleoyl-sn-Glycero-3-Phosphoethanolamine (DOPE), 1,2-dioleoyl-sn-Glycero-3-Phospho-L-Serine (DOPS); cholesterol (Chol), 1,2-dioleoyl-sn-Glycero-3-Phosphoinositol-4,5-Bisphosphate (PI(4,5)P2) and 1,2-dioleoyl-sn-Glycero-3-Phosphoethanolamine-N-(Lissamine Rhodamine B sulfonyl) (Rh-DOPE) were purchased from Avanti Polar Lipids, Inc. (Alabaster, Ala., USA)N-decane was purchased from Fisher Scientific. 8-Hydroxypyrene-1,3,6-Trisulfonic Acid (HPTS) Trisodium Salt, hexane and gramicidin A from *Bacillus aneurinolyticus* (*Bacillus brevis*) were purchased from Sigma-Aldrich (St. Louis, Mo., USA) and Invitrogen (Carlsbad, Calif. USA)). Short single-stranded DNA oligonucleotides (81-nt) were purchased from Integrated DNA Technologies, Inc. (Coralville, Iowa, USA).

CNT Cutting.

To remove amorphous carbon and impurities from the CNT sample, 1.6 to 2 mg of as-received CNTs were first purified in a thermal gravimetric analysis (TGA) system (Q5000 IR TGA-MS, TA Instruments, New Castle, Del. USA)) in 25 mL/min stream of air while the temperature was ramped at a rate of 5° C./min from 20° C. to 450° C. In a typical CNT porin preparation procedure, 2 mL of DOPC (10 mg/mL in chloroform) was added to a 20 mL glass vial and the solvent was evaporated using a V10 evaporator (Biotage, Uppsala, Sweden) to form a thin lipid film on the walls of the glass vial. 1.6 mg of purified CNTs and 20 mL DI water (Milli-Q, Millipore, Boston, Mass. USA) were added to the same vial. Following 1 hr. of bath-sonication (Model 1510, Branson Ultrasonics, Danbury, Conn., USA), the sample was probe-sonicated for 16 hrs (Model VC 100, Sonics & Materials Inc., Newtown, Conn., USA) at 100 W power delivered in 3 s. pulses separated by a 1 s. pause. During sonication, the vial was continuously cooled in an ice-water bath and, if necessary, DI water was added to compensate for loss in sample volume due to evaporation.

Purification and Incorporation of CNT Porins into Liposomes.

To separate the cut CNTs from the uncut nanotube material, 10 mL of suspension processed by sonication cutting was added to a 15 mL centrifuge tube and centrifuged at 4000 rpm for 1 hr using Allegra X22 centrifuge (Beckman-Coulter, Indianapolis, Ind., USA). The dark supernatant solution containing lipid-stabilized cut CNTs was stable and could be dried and re-suspended in DI water, suggesting that the lipid coating helped to prevent the aggregation of the cut CNTs.

To incorporate CNTs into DOPC liposomes, a 0.2 mL aliquot of 10 mg/mL DOPC in chloroform was added to a 20 mL glass vial and the solvent was evaporated to leave a dried lipid film. 1 mL of purified CNT/DOPC complex solution was added to the vial and the mixture was allowed to hydrate for one hour. The solution was then extruded through a 200 nm-diameter pore polycarbonate membrane using a hand-held Mini-Extruder device (Avanti Polar Lipids) for 10 cycles.

Cryo-TEM Specimen Preparation and Instrumentation.

5 µL aliquots of liposomes incorporating CNT porins (as well as vesicle-only control samples), were placed onto 200 mesh carbon-stabilized lacey-Formvar copper grids (#01881, Ted Pella, Inc., Redding, Calif. USA), manually blotted with filter paper, and plunged into liquid ethane at liquid nitrogen temperature. For control studies of isolated cut and uncut CNTs with and without lipids, 5 µL aliquots were placed on 200 mesh carbon-stabilized Formvar-film copper grids (#01800, Ted Pella, Inc.), blotted with filter paper and then air-dried. All TEM grids were glow discharged. Samples were transferred to a JEOL-3100-FFC transmission electron microscope equipped with a field emission gun (FEG) operating at 300 kV, an Omega energy filter, a Gatan 795 4K×4K CCD camera (Gatan Inc., Pleasanton, Calif., USA) mounted at the exit of an electron decelerator operated at 200 kV resulting in images formed by a 100 kV electron beam at the CCD, and a cryo-transfer stage. The stage was cooled with liquid nitrogen to 80 K during the acquisition of all datasets.

Cryo-TEM Image Acquisition and Analysis.

Images were recorded at a nominal magnification of 40,000× giving a pixel size of 0.14 nm at the specimen, either without camera binning or using a camera binning factor of two. Underfocus values ranged from 2±0.25 µm to 3.6±0.25 µm, and energy filter widths were typically around 30 eV. The surveys of cryo samples and the selection of suitable targets were performed in low-dose defocused diffraction mode. Images were acquired under low-dose conditions, with doses of ~20-40 $e^-Å^{-2}$ per image. For the control samples of cut and uncut CNTs with and without lipids, images were acquired at 80,000× giving a pixel size of 0.07 nm at the specimen. Several dozen images were acquired with defocus values ranging from minimum contrast to 2 µm underfocus. Through-focus series were also acquired. Images acquired at 2 µm underfocus with camera binning factor of two, giving a pixel size of 0.14 nm, agree well with the images obtained for the cryo vesicle-CNT samples acquired at the same defocus. The package of imaging tools Priism (http://msg.ucsf.edu/IVE/) was used for noise reduction and contrast enhancement. ImageJ 1.38× software (NIH, http://rsb.info.nih.gov/ij/) was used for analysis and measurements of the 2D image projections. Since the images represent a 2D projection of a 3D structure the measured CNT length values represent the lower boundary estimate of the true CNT lengths. To characterize the length- and tilt-angle-distribution (FIGS. 1D and 1E, respectively) of short CNTs before and after insertion into lipid bilayers, Applicants manually measured the length of identifiable individual CNTs from a series of high-resolution TEM images (FIG. 1C, FIGS. 5A-5M, FIG. 6A). Only CNTs with relatively high signal-to-noise were selected for analysis.

Conventional TEM Specimen Preparation and Imaging.

Control samples of isolated cut and uncut CNTs were also investigated (FIGS. 5A, 5B, 6B, 6C) with a room-temperature stage using a Philips CM300 TEM, operated at 300 kV with the field-emission gun extraction voltage set at 4.2 kV. Specimens were prepared by first dispersing the CNTs in ethanol using 30 minutes of bath sonication, and then drop-casting onto lacey-carbon TEM copper grids. The average diameter for the uncut CNTs was 1.51±0.21 nm, as measured over a dozen individual tubes.

Atomic Force Microscopy (AFM) Imaging.

Figure 7:
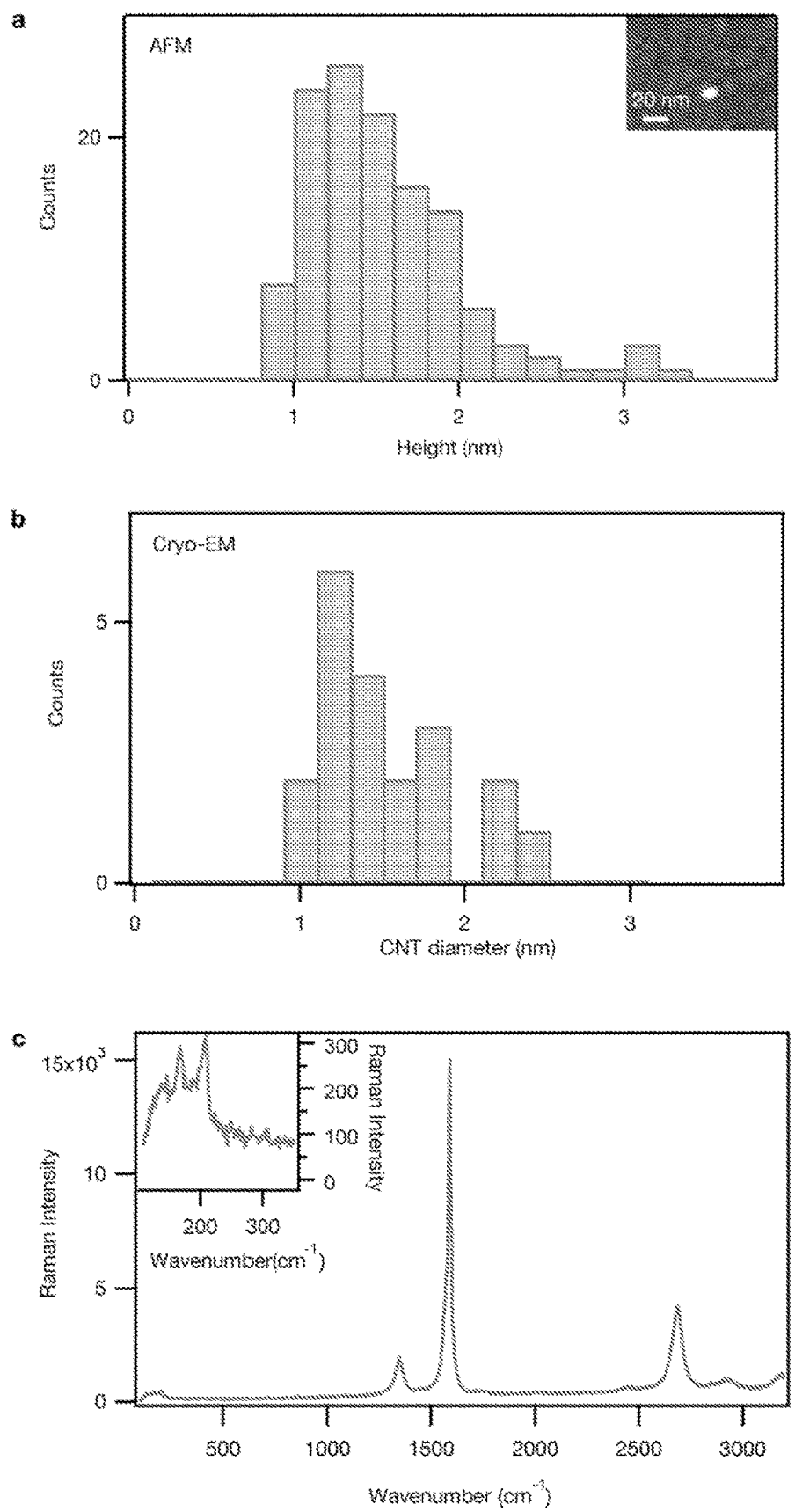
FIGS. 7A-7C: Characterization of CNT porins. A. Histogram of the height (diameter) of short CNT fragments measured with AFM. Most CNT porins show diameters between 1 and 2 nm. Inset shows a high-magnification AFM image of a single CNT on a bare mica surface. B. Histogram of the diameters of CNT porins inserted into the lipid vesicles measured by Cryo-TEM. C. Raman spectrum for the short-CNT/lipid complex after 16 hours of sonication-assisted cutting. Inset shows a magnified view of the radial breathing mode region of the CNT spectrum (150-300 $cm^{-1}$).

AFM imaging was performed using a Multimode Nanoscope IIIA, Nanoscope VIII AFM (Digital Instruments, Santa Barbara, Calif., USA), and Asylum Research MFP-3D (Asylum Research, Santa Barbara, Calif., USA), both operating in tapping mode. For imaging in air, Applicants used silicon tips (PPP-FMR, Nanosensors GMBH, Germany) with nominal probe radius of less than 7 nm, force constant of 2.8 N/m, and resonance frequency of 75 kHz. 10 µL of purified CNT solution was deposited onto freshly cleaved mica pre-treated with poly-L-lysine solution (Ted Pella) to facilitate adsorption of negatively-charged CNTs, allowed to incubate for 2 minutes, rinsed with DI water, and dried with nitrogen. AFM images typically represent a true height (diameter) value of the CNTs, and the average CNT height observed in the AFM images, 1.54±0.44 nm (FIG. 7A), matches the CNT diameter value determined from the cryo-TEM and Raman measurements (FIGS. 7B, 7C, respectively).

Raman Spectroscopy.

A droplet of CNT/DOPC suspension was placed onto a glass cover slip, dried and placed into a Renishaw micro-Raman spectrometer (Renishaw, Hoffman Estates, Ill. USA) using 488 nm laser illumination. The Raman spectrum for short CNTs showed the typical CNT bands at 1600 $cm^{-1}$ (G band) and ~1300 $cm^{-1}$ (D band), and show a G/D ratio of 8 (FIG. 7C), indicating that the CNT walls maintain a graphitic structure after sonication cutting.

Proton Transport Assay.

To prepare the CNT-containing liposomes loaded with a pH-sensitive fluorescent dye, a 0.1 mL aliquot of 10 mg/mL DOPC in chloroform was added to a 20 mL glass vial, and dried into a film by evaporating the solvent. 1 mL of CNT porin (1 mg/mL) solution in 1 mM HPTS and 150 mM KCl (titrated to pH 8), were added to the dried lipid film, allowed to rehydrate for 1 hour and then extruded through a 200 nm diameter pore polycarbonate membrane. For preparation of a control sample, 0.2 mL aliquot of 10 mg/mL DOPC in chloroform was dried to a film, rehydrated with 1 mL of 1 mM HPTS and 150 mM KCl (pH=8), and extruded the same way. Unencapsulated external dye was removed using a size exclusion chromatography (SEC) column packed with Sepharose CL-6B resin (Sigma-Aldrich). After Applicants inserted the CNT porins into the liposome walls Applicants did not observe any leakage of the HPTS dye from the liposomes, indicating that the CNT porins were impermeable to HPTS. All solutions used for these experiments contained a 150 mM isosmotic concentration of background KCl electrolyte to ensure the absence of osmotic pressure gradients.

HPTS dye emission (ex. 450 nm, em. 514 nm) was monitored using a FluoroMax-4 fluorometer (Horiba Inc. Albany, N.Y., USA). For kinetic measurements, 0.2 mL CNT-liposome sample (or 0.2 mL control liposome sample) was added to the cuvette containing 2 mL of 150 mM KCl (pH=3). Solution was continuously stirred with a magnetic stir bar during measurements.

Osmotic Pressure-Induced Liposome Size Change Measurement.

0.2 mL of 10 mg/mL DOPC solution in chloroform was added to a vial and dried to a film using a Biotage V-10 evaporator. 1 mL of CNT porin solution was added to the vial and extruded through polycarbonate filter membrane with 200 nm diameter pores using a hand-held extrusion device (mini-extruder, Avanti Polar Lipids). A control sample was prepared in a similar way, except that 0.3 mL of the DOPC solution was used to prepare a lipid film and water was added instead of CNT porin solution.

Hydrodynamic radius of the liposomes was measured using a dynamic light scattering (DLS) setup (Zetasizer, Malvern Instruments, Malvern, UK). In a typical measurement, Applicants mixed 10 µL of the liposome solution with 70 µL NaCl solution of known concentration in a low-volume cuvette cell (Malvern Instruments).

Single Channel Recordings of CNT Porin Conductance.

A supported lipid bilayer was formed over a 200 µm diameter aperture in a Teflon film partition installed in a two-chamber BLM cell (Eastern Scientific LLC, Rockville, Md., USA) using a painting technique (29). The trans-chamber (connected to ground Ag/AgCl electrode) and cis-chamber (connected to a reference electrode Ag/AgCl) were filled with 2 mL and 0.2 mL conducting buffer (KCl or NaCl with 5 mM HEPES, pH 7.4) respectively. During the measurement 2 µL solution of DOPC liposomes containing CNT porins or the stock CNT porin solution was added to the cis-chamber.

A holding potential between −200 mV to 200 mV was applied to the reference electrode, and the trans-membrane current signal was recorded by a patch clamp setup, which consisted of an Axopatch 200B patch clamp amplifier and an Axon DigiData 1322A analog-digital converter (Axon Instruments, Milpitas, Calif., USA) connected to a computer system running Clampex 10.3 software (Axon Instruments). Traces were acquired at a sampling frequency of 10 kHz-100 kHz and were low band-pass filtered at a frequency of 5 kHz or 2 kHz to increase signal-to-noise ratio. The data were analyzed and exported using PClamp 10.3 software (Axon Instruments), and further analyzed using Origin Pro 8.0 and Igor Pro 6.31.

As a positive control, the conductance of Gramicidin channels was measured using the following procedure: 0.1 mg Gramicidin A was incubated with 200 µL of the DOPC liposome solution (150 mM KCl, 4 mg/mL lipid concentration, pH 7.4). After a lipid bilayer was formed over the testing setup aperture (in the presence of 1 M KCl solution in both chambers), 2 µL of gramicidin A/liposome solution was added into the cis-chamber and the conductance traces were recorded using a transmembrane potential of 75 mV. The conductance measured for gramicidin was 0.058±0.008 nS, which is close to the reported values 0.0459±0.005 pS[30].

DNA Translocation Measurements.

DNA translocation measurements. Applicants used a similar setup and sample preparation technique to that described in the preceding section. ssDNA oligonucleotide (5'-/5Phos/GCG GCC GCT ACT AGT CTT ACC GCC ACC CAG AGG GCC ATA ACG GGT ACG GTA TTG GCT TAC ACG GTT ACG CAG ACG CTG TAC-3', 81 nt length (SEQ ID NO: 1)) was pre-mixed into the solution (1 M KCl, pH 7.4) in the cis-chamber to a final concentration of 100 pM. After a planar lipid bilayer was formed, 2 µL of CNT-containing liposomes was added into the solution in the cis-chamber by pipette. A holding or ramping potential of 50 mV maximum amplitude was applied across the bilayer. For the control experiment no ssDNA was added to the chambers. Translocation events from current traces of a total of 338 s duration were counted either manually or using custom-written software in Igor Pro (Wavemetrics, Inc., Lake Oswego, Oreg., USA).

Cell Culture and on Cell Patch-Clamp Measurements.

CHO and HEK 293T cells have been cultured according to the prescribed protocol (ATCC website), at 37° C., 5% $CO_2$, in 25 $cm^2$ flasks, in DMEM (HyClone SH30243.01 High Glucose) supplemented with Gentamicine antibiotic (5 mg/L) and 10% serum (DE14-801F, Lonza, Allendale, N.J., USA). These cells are known for low endogenous channel activity and, consequently, widely used for heterologous expression of ion channels. 24 hours prior to the experiment, the cells were plated in 35 mm Petri dishes (with plastic bottom observation window, 35 mm low µ-Dish cat #80136, Ibidi, Martinsried, Germany) using PBS without $Ca^{2+}/Mg^{2+}$ (D8537, Sigma, St. Louis, Mo., USA). For the patch-clamp experiment the culturing media was substituted with external solution (PBS with $Ca^{2+}/Mg^{2+}$, Sigma, D8662), the experiments were conducted within the next 45 minutes, at room temperature.

Patch-pipettes were produced from borosilicate glass (GB150-10, Science Products, Hofheim, Germany) using a Sutter P-2000 puller (Sutter Instruments, Novato, Calif., USA) and filled with the solution containing (in mM): 150 KCl, 10 HEPES, and 1 EDTA pH 7.0; the pipette resistance was 3-5 MOhm. CNT porin solution was added to the pipette solution before each experiment. Applicants used 0.15% dilution of the CNT porin stock solution in the pipette buffer, a higher amount of the CNT interfered with the gigaseal formation. The data were obtained and pre-processed using EPC10 patch-clamp amplifier (HEKA Electronik, Lambrecht/Pfalz, Germany), at 5 kHz sampling rate with the 2.9 kHz internal filter of the EPC10. At the beginning of each record Applicants applied a series of holding potential steps (from −60 mV to +60 mV) to estimate the reversal potential. For data acquisition, Applicants used cells with approximately symmetric current response (FIG. 14E), using −30 mV and −60 mV holding potentials which induced minimal endogenous channel activity. Stable conductance levels were detected using FITMASTER software (HEKA). The background (reference) conductance was determined from an all-point histogram. The Gaussian fits to the conductance histograms for HEK293T cells (FIG. 4B, lighter grey bars, lighter grey line) give the peak values of 68.1±0.8, 122.7±1.0, 177.8±2.1, 223.4±2.7 pS. For CHO cells (FIG. 4C, lighter grey bars, darker grey solid line) the peak values were 67.6±1.4, 130.8±1.3, 195.3±1.1, and 255.3±10 pS.

Patch-Clamp Measurements on Planar Lipid Bilayer and Giant Unilamellar Vesicles.

Planar lipid bilayers were prepared using a similar methodology as above, based on the modified Montal-Mueller "painting" procedure described elsewhere (3). The bilayers were produced from 20 g/L solution of lipids in squalane; charged membranes contained (in mol %): 28% DOPC, 25% DOPE, 30% Chol, 15% DOPS, and 2% PIP2; non-charged membranes contained (in mol %) 30% DOPC, 20% DOPE, and 30% Chol. Membranes were formed on 300× mesh copper TEM grids (Pelco®, 1GC300) mounted on the bottom of the Petri dish using adhesive spacers (Grace BioLabs Inc., OR, USA) as described previously (4). Grids were pretreated with the appropriate combination of lipids dissolved in 1:1 mol/mol octane:decane, 20 g/L$^{31}$. The bilayers were formed in the working Buffer 1, containing (in mM): 150 KCl, 10 mM Hepes, and 1 mM EDTA, pH 7.

Giant unilamellar vesicles (GUVs) were produced by spontaneous swelling of lipid films deposited on silica beads (32). The "charged membrane" composition was used, supplemented with 0.5 mol % of Rh-DOPE for fluorescence microscopy detection of GUVs. The GUV preparation was modified to allow for the CNT incorporation into lipid films prior to GUV formation. Briefly, the initial lipid film (total 0.05 mg of the appropriate lipid mixture in chloroform/methanol (9:1 vol/vol) mixture was formed in a round bottom flask using rotary evaporator. 1 mL of CNT stock solution was added and mixed thoroughly to resuspend the lipid film. The mixture was dried in vacuum and then 50 mL of chloroform was added and rapidly dried in a rotary evaporator in order to form a homogeneous lipid-CNT film. 10 mL of distilled water was added for 30 min pre-hydration of the film at 50° C. The film was vortexed and the resulting mixture was added to solution containing 40 mm plain silica beads (Corpuscular Inc. Cold Spring, N.Y., USA): A small (2.5 mL) drop of CNT/lipid mixture was added to a 0.5 mL drop of the bead solution (10% vol/vol) deposited on Teflon film. The drops were dried in a vacuum chamber drier (15 min, room temperature). CNT-GUVs formation was detected within 10 min after the addition of 300 mM sucrose buffer at room temperature.

CNT-GUVs remained attached to the beads transferred to the observation chamber (with a glass-bottom observation window pretreated with bovine serum albumin as described previously)(32) containing Buffer 1. The chamber was mounted in an inverted microscope equipped with Andor iXon+ camera (Andor Technology, Belfast, UK) operating with the ImageJ-µManager open source software (33) and LUCPFLF 40×/0.60NA objective. 550/590 nm excitation/emission wavelengths were used. Conductance measurements were performed 30 min after the GUV transfer to the Buffer 1 to allow for the equilibration between the GUVs' interior solution and the buffer.

For patch-clamp experiments on planar bilayers and GUVs Applicants used borosilicate glass pipettes (Science Products, GB150-10) filled with Buffer 1. The pipette resistance was 3-5 MOhm and 0.15 to 0.30% of the CNT porin solution was added to the pipette solution. Experiments were conducted at room temperature. The pipette approach to the bilayer and formation of gigaseal was performed as described earlier (31, 32). The patch conductance was measured at +50 and −50 mV holding potentials using an Axopatch 200B (Axon Instruments) amplifier and a PC-44 acquisition board (Signalogic). The sampling frequency f was 1 kHz and signals were passed through 8-pole Bessel filters (Frequency Devices) set at f/2 corner frequency. The data were processed using FITMASTER software (HEKA).

Experimental Discussion

The molecular transport in carbon nanotubes (CNT) have been explored in modeling (7,8) and experimental (4-6) studies and simulations have predicted that a nanotube with a length comparable to the thickness of a lipid bilayer membrane could self-insert into the membrane (9,10). Although there is evidence of functionalized CNT penetration through lipid membranes and cell walls (11,12), formation of transmembrane CNT pores has remained underexplored (13). Applicants created short CNTs, which can form such pores, using sonication-assisted cutting (14) of purified long CNTs with an average inner diameter of 1.51±0.21 nm in the presence of 1,2-dioleoyl-sn-glycero-3-phosphocholine (DOPC) lipid (FIG. 1A). This procedure produced a stable dark suspension (FIG. 1B, inset) containing short CNTs stabilized by the lipid coating (see Materials and Methods for transmission electron microscopy (TEM) images of uncut and cut CNTs (FIGS. 5A-5M), CNT length distributions (FIGS. 6A-6C), and CNT diameter distributions (FIGS. 7A, 7B). Raman spectroscopy confirmed that the cutting procedure preserved the inner diameter and rolled-up graphene-sheet structure of the nanotube (FIGS. 7A-7C). High-resolution TEM images of the purified cut CNTs (FIG. 1B, FIGS. 5A-5M) also indicate the presence of a significant population of short CNT fragments in the 5-15 nm range (FIG. 1D, FIGS. 6A-6C).

Figure 8:
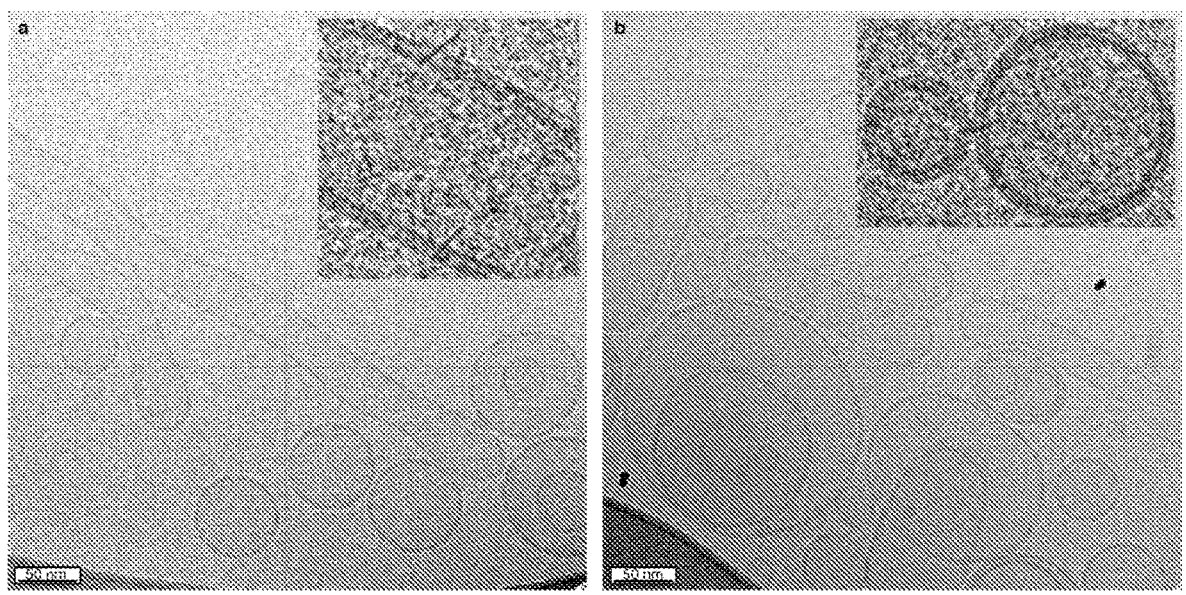
FIGS. 8A-8B: Cryo-TEM images of CNT-liposome complexes. A, B. Original large field-of-view images with a magnified view of the selected structures with colored lines highlighting the lipid bilayer and CNT porins.
Figure 9:
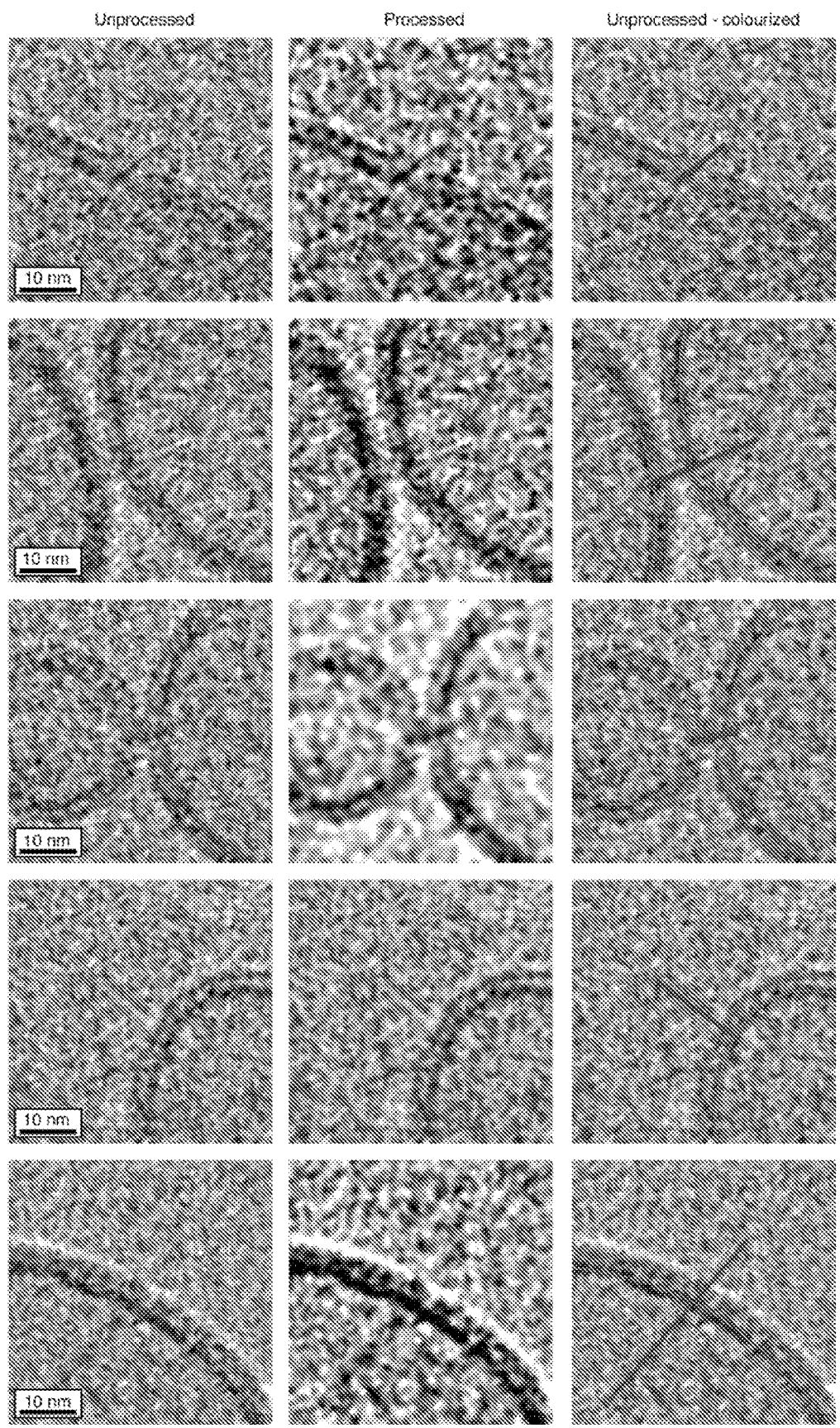
FIG. 9: High magnification cryo-TEM imaged of CNT-liposome complexes. Panels (left to right) showing unprocessed, processed, and colorized examples (shown in grey scale here).

Cryogenic TEM (cryo-TEM) images of the CNT porins reconstituted into 200 nm diameter liposomes (see Materials and Methods) reveal short CNT fragments inserted into the lipid membrane and spanning both membrane leaflets (FIG. 1C, and FIGS. 8A-8B for wider field-of-view cryo-TEM images, and FIG. 9 for higher-magnification images). Because the graphitic structure and functionality of short CNTs resembles the β-barrel structure of porins—water-filled channels in biological membrane, the structures were termed "carbon nanotube porins". Cryo-TEM images also show that the presence of CNT porins does not affect the integrity of the lipid bilayer. Statistical analysis of cryo-TEM images reveals a relatively wide length distribution of the inserted CNTs (FIG. 1D), indicating that the insertion was not selective to a particular length. CNT porins strongly prefer the perpendicular orientation to the membrane plane with the majority of the nanotubes tilting only 15 degrees or less from the membrane normal (FIG. 1E). This observation is surprising, since molecular dynamics (MD) simulations predicted that CNTs longer than the thickness of the bilayer (4.6±0.2 nm for the DOPC membranes) should tilt to maximize the interactions of the hydrophobic bilayer core with the hydrophobic CNT walls (9). Finally, for most CNT porins at least one end of the CNT abutted the hydrophilic head groups of the lipid bilayer, allowing for energetically favorable interactions of the hydrophilic groups on the porin rim with the hydrophilic lipid headgroups.

CNT porins enable efficient transport of chemical species across several types of lipid membranes. To demonstrate proton transport through the CNT porins Applicants placed liposomes containing an encapsulated pH-sensitive dye (8-hydroxypyrene-1,3,6-trisulfonic acid trisodium salt, HPTS) at pH=8.0 into isosmotic buffer solution at pH=3.0. In the absence of the CNT porins, the background proton leakage through the vesicle membrane lead to a slow HPTS fluorescence decay with a characteristic timescale of 187 s (FIG. 1F). Conversely, samples that contained CNT porins in the bilayer showed much faster initial florescence decay with a 35 s timescale, indicating the opening of a significant second pathway for protons to enter the vesicle lumen. The decay kinetics represented a sum of two exponential terms, with the second term matching the 187 s timescale obtained in a control experiment (FIG. 1F, inset), indicating that a small subpopulation of the liposomes did not contain CNT porins.

To explore transport through the CNT porins further, Applicants placed liposomes filled with pure water into dilute NaCl solutions and monitored liposome size changes resulting from osmotically-driven water expulsion (15) using dynamic light scattering (DLS). Control liposomes without CNT porins showed minimal (<2.3%) size changes, whereas liposomes incorporating CNT porins quickly shrank by up to 20% (FIG. 1G). CNT porin vesicle shrinkage depends strongly on the ionic strength of the outside solution, being highest at low ionic strength and reducing dramatically at high ionic strengths to approach values measured for the control samples. Such behavior is understandable: at pH=7.0 the ring of negatively charged carboxylic acid groups at the CNT porin entrance creates an electrostatic barrier for the anion passage and slows down the ion leakage into the liposome lumen, allowing the osmotic pressure to shrink the vesicles (FIG. 1G, inset). At higher ionic strength these entrance charges are screened, allowing ions to pass through the CNT pore and neutralize the osmotic gradient. Indeed, the transition from high to low ion rejection in our measurements occurs at the same Debye length range (6-7 nm) that Applicants previously observed for bulk CNT membranes (16), confirming that the observed effects are closely related to ion diffusion through the CNT pores.

Figure 2:
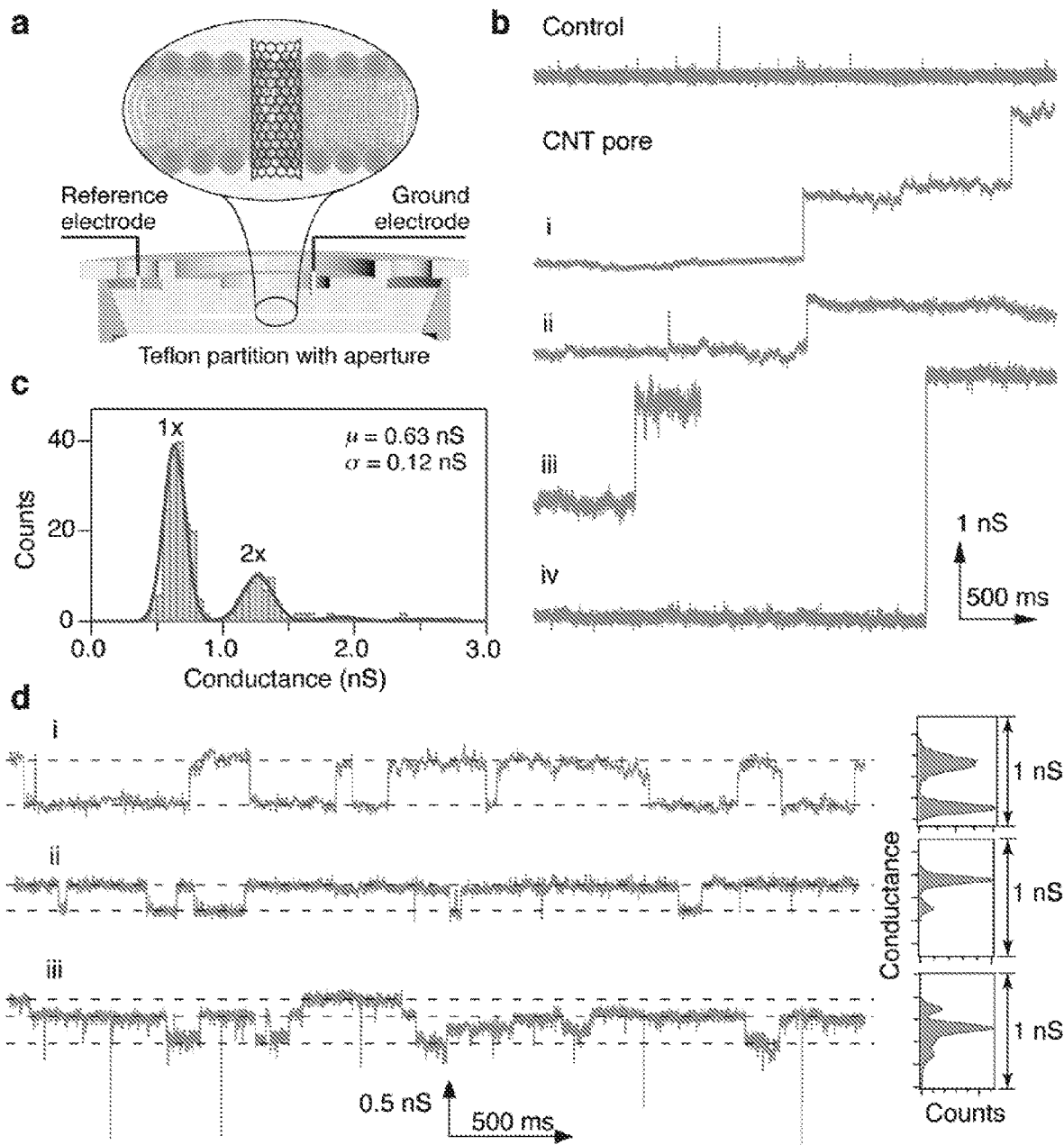
FIGS. 2A-2D: Transport through individual CNT porins. A. Setup for single-channel recording of CNT porin conductance. B. Conductance traces showing single (i, ii) and multiple (iii, iv) CNT porins incorporation into the lipid bilayer. Control trace was recorded in absence of CNTs. C. Histogram of CNT porin conductance values (n=236). Solid line is a sum of two Gaussian peaks where the position and width of the second peak are determined from the position, $\mu$ and width, of the first peak as $2\mu$ and $\sqrt{2}\sigma$. D. Conductance traces and normalized conductance histograms showing stochastic "gating" transitions for one (i, ii) and two (iii) CNT porins.

Applicants observed spontaneous membrane incorporation and characterized transport properties of individual CNT porins using single channel conductance measurements (FIG. 2A). When CNT porins were added to the top chamber, the bilayer conductance showed a series of characteristic amplitude jumps (FIG. 2B), indicating membrane incorporation events. Conductance traces contained a mixture of well-separated events and multiple steps corresponding to a relatively quick succession of incorporation events. The histogram of conductance step values (FIG. 2C) shows clear evidence of quantization with the first peak corresponding to the 0.63±0.12 nS value for a single CNT pore conductance and a subsequent peak at exactly double that value. Occasionally, conductance jumps were recorded at higher multiples of the single pore conductance value, but the frequency of those events was low.

Figure 10:
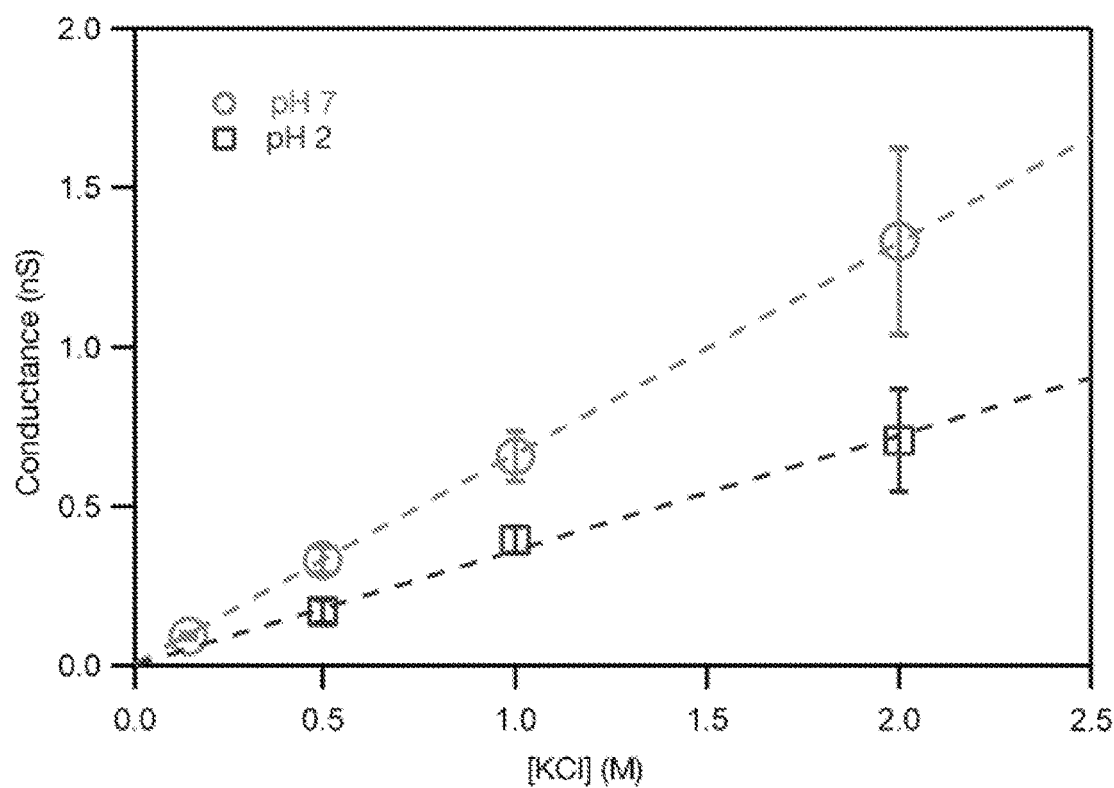
FIG. 10: Single CNT porin conductance at different electrolyte concentrations. Plots of the average single CNT porin conductance at different values of background electrolyte (KCl) concentrations at pH=7 (circles) and pH=2 (squares). Error bars: s.d. (pH=7: 0.15M,n=6, 0.5M,n=161; 1M,n=39; 2M,n=8. pH=2: 0.5M, n=18; 1M, n=3; 2M, n=36). The slopes of the linear fit through the data (dashed lines) correspond to 0.66 nS/M at pH=7 and 0.36 nS/M at pH=2.
Figure 11:
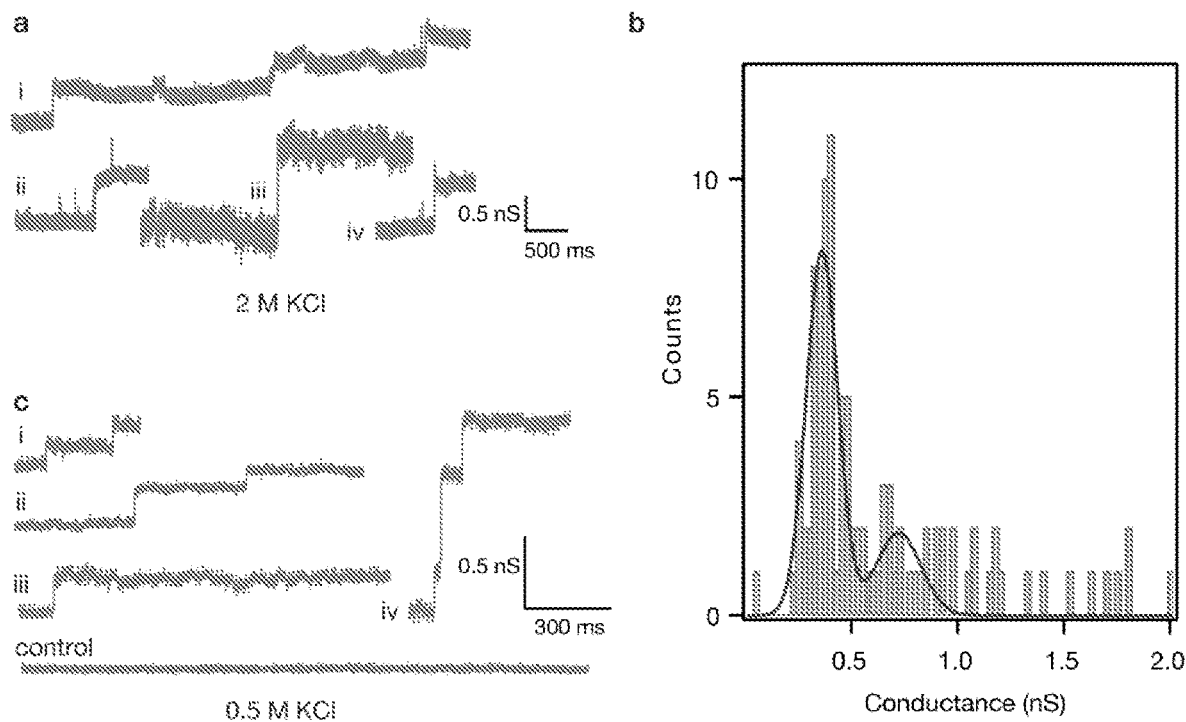
FIGS. 11A-11C: Single CNT porin conductance at pH=2. A. Representative conductance traces showing individual CNT porin incorporation at pH=2 and 2 M KCl background electrolyte concentration. B. Histogram of conductance values measured for 109 individual CNT channel incorporation events (n=109). Solid line corresponds to the fit of the data to a distribution expected for multiple channel incorporation, where the position and width of the second peak are determined from the position, μ (0.36±0.006 nS) and width, μ (0.10±0.008 nS) of the first peak as 2μ and √2σ. C. Representative conductance traces showing individual CNT porin incorporation at pH=2 and 0.5 M KCl background electrolyte. Control trace shows a conductance trace collected at the same conditions without adding CNT porins.
Figure 12:
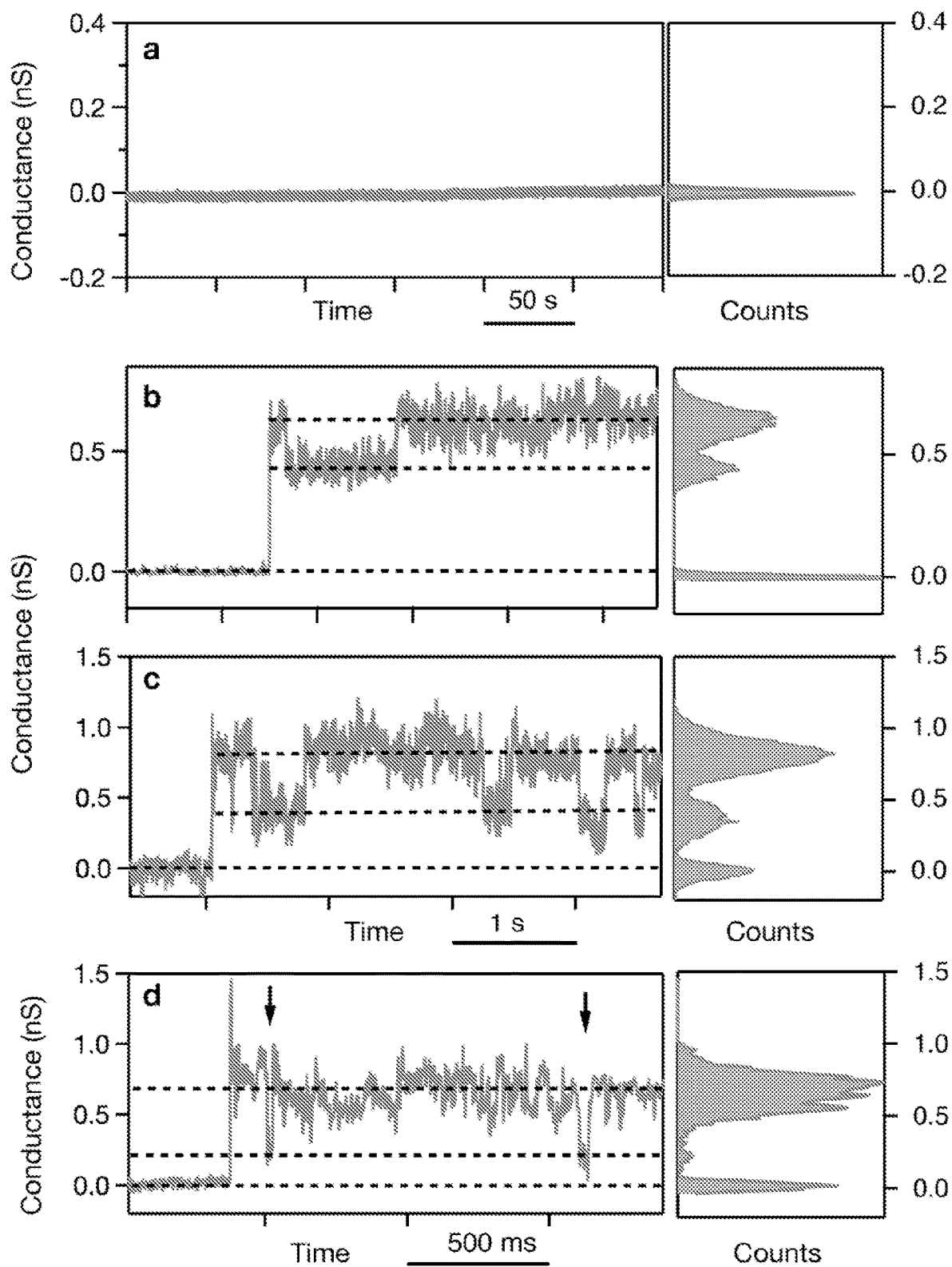
FIGS. 12A-12D: Representative traces and corresponding current level histograms of CNT porin incorporation, gating and DNA translocation in lipid bilayers at pH=7. A. Control conductance trace recorded in absence of CNT porin. Although only the first 5 minutes are shown, the current level remained stable for up to 80 minutes. n=3·10⁶. B, C. Conductance traces and histograms showing single CNT porin incorporation events and subsequent current fluctuations between gating sub-levels. n>5·10⁴. D. Trace and conductance value histogram showing CNT poring incorporation event and subsequent two DNA translocation events (indicated by black arrows). n=3·6·10⁵) The peaks on the histogram correspond to 0.01 nS for pre-incorporation baseline, 0.22 nS for DNA blockade, and 0.67 nS for open pore conductance, which gives the DNA blockade of 0.45 nS and a blockade ratio of 67%. Dashed lines are added to all traces as a guide to the eye.

CNT porin conductance scaled linearly with salt concentration in the 0.5 M-2 M range both at neutral pH and at pH=2 (FIG. 10), strongly suggesting that the dominant conductance mechanism through the CNT porin is ionic. The unitary conductance of a CNT porin at pH=2 was reduced by almost a factor of 2 compared to neutral pH, from 0.63 nS to 0.33 nS (FIG. 11B). This observation rules out proton conductivity as the dominant current-carrying mechanism in these pores and suggests that the conductance of the CNT porins is sensitive to the charges at the pore mouth (which are neutralized at pH=2). Similar decrease in channel conductance at acidic pH due to the changes in the charge state of the pore residues has been reported for OmpF porins (19).

For less than 30% of the CNT porins the conductance signal oscillated between "open" and "partially-closed" sub-states after insertion, showing distinct peaks in the histograms of the trace amplitude (FIG. 2D). Notably, Applicants did not observe these low conductance sub-states at pH=2 (FIGS. 11A, 11C). Computer simulations of pore insertion into lipid bilayers indicate that rapid removal and re-insertion of the CNT porins from the bilayer cannot cause these oscillations (9). The ionic nature of the conductance in CNT porins argues against the possibility that the oscillations originate from the ion blocking of the proton-based current as previously reported for macroscopically-long CNT channels (6). Transient blocking by nanoprecipitation (20) requires the presence of divalent ions and produces distinct triangular shaped blockades different from the ones Applicants observed. Another possible cause, spontaneous wetting/dewetting transitions in hydrophobic nanopores (21), should have produced a clear zero-conductance "off" state; however, this system frequently shows only a partially-blocked low conductance sub-state (FIGS. 11B, 11C), suggesting that the CNT interior remains filled with water (8).

Conductance oscillations in CNT porins are similar to the stochastic "gating" behavior of biological ion channels. Unlike biological channels, however, where conformation transitions are commonly invoked as a cause of conductance sub-states, CNT porins contain no movable parts and the entire pore structure is rigid. Similar transitions have been reported previously for ion-track-etched polyethylene terephthalate solid-state nanopores (22) and glass-polymer nanogaps (23). One possibility is that these sub-states represent a spontaneous transition between ionic-penetration and ionic-exclusion states as predicted by Palmeri and co-workers (24) for weakly charged or neutral nanopores embedded in a dielectric medium. This model predicts the existence of low-conductance sub-states for charged nanopores and on/off transitions for uncharged pores. Consistent with this prediction, the low conductance states disappear at pH=2. Although Applicants find some parallels with the behavior reported for OmpF porin channels (19), further experimental work is necessary to understand the detailed nature of conductance fluctuations.

Figure 3:
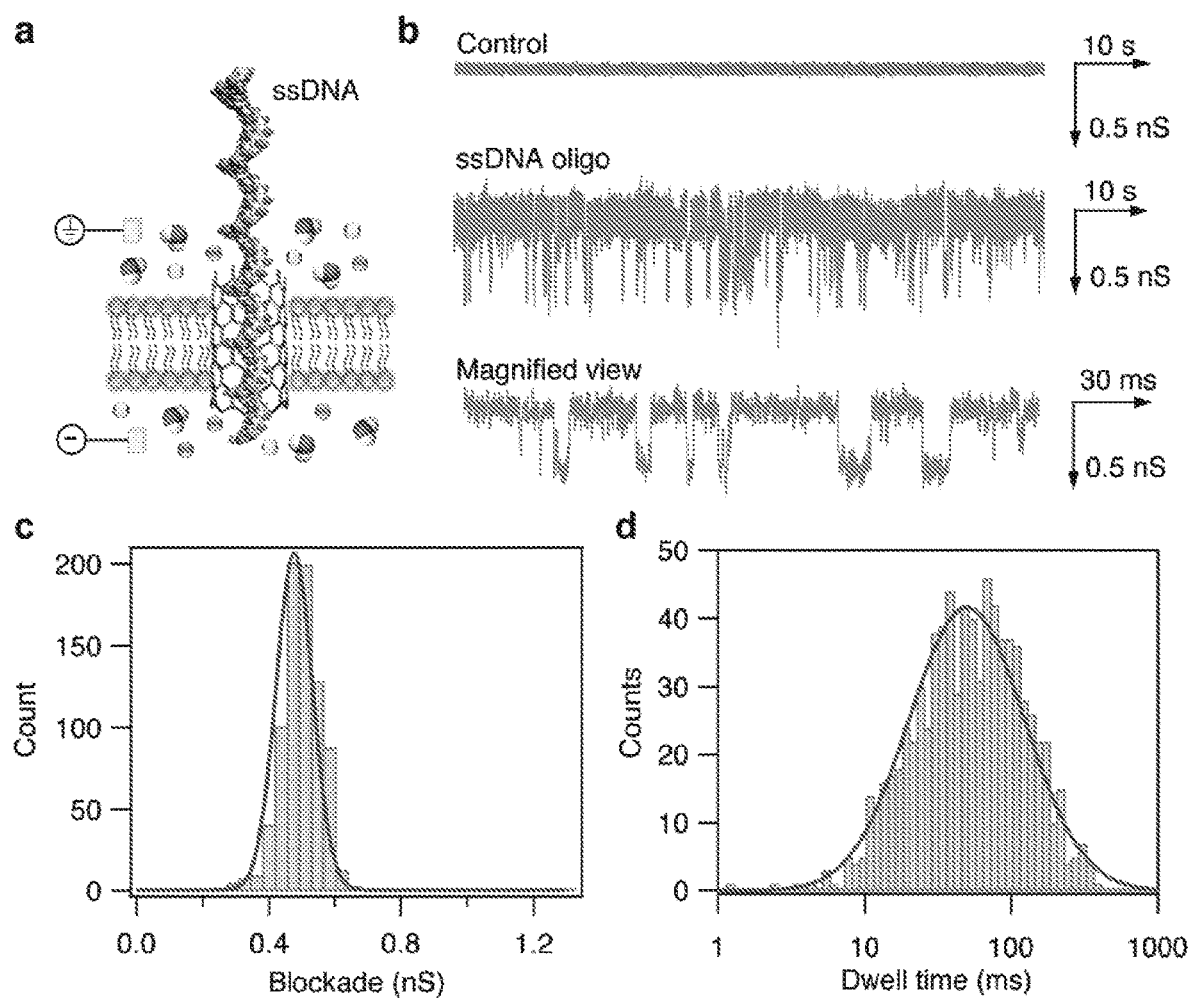
FIGS. 3A-3D: DNA translocation through CNT ion channels. A. Schematic showing the translocation of single-stranded DNA through a CNT porin in the lipid bilayer. B. Current trace showing multiple transient blockades caused by 81-nt ssDNA translocation through the CNT channel. The applied voltage was −50 mV. C, D. Histograms of the ssDNA conductance blockade levels and dwell times. (n=806).

Applicants next explored electrophoretic translocation of macromolecules through individual CNT porins. When short 81-nucleotide(nt)-long single-stranded DNA (ssDNA) oligomers were present in the trans-chamber of this system (FIG. 3A) Applicants observed rapid conductance blockades that corresponded to the translocations of individual ssDNA strands through the CNT pore (FIG. 3B). Statistical analysis indicated that conductance blockade values followed a normal distribution centered at 0.48±0.08 nS (FIG. 3C). This value is between the 0.8 nS blockades reported for wild-type α-haemolysin pores (25), which have a similar diameter to CNT porins, and the 0.3 nS blockades reported for a hybrid α-haemolysin/solid-state nanopore structure (26). DNA translocation dwell times followed a log-normal distribution (FIG. 3D) centered around a value of 53 ms, which corresponds to an average DNA translocation speed of 1.5 $nt \cdot ms^{-1}$. This value is comparable to the speed achieved by biological nanopores and falls into a range suitable for DNA analysis applications (27).

Figure 4:
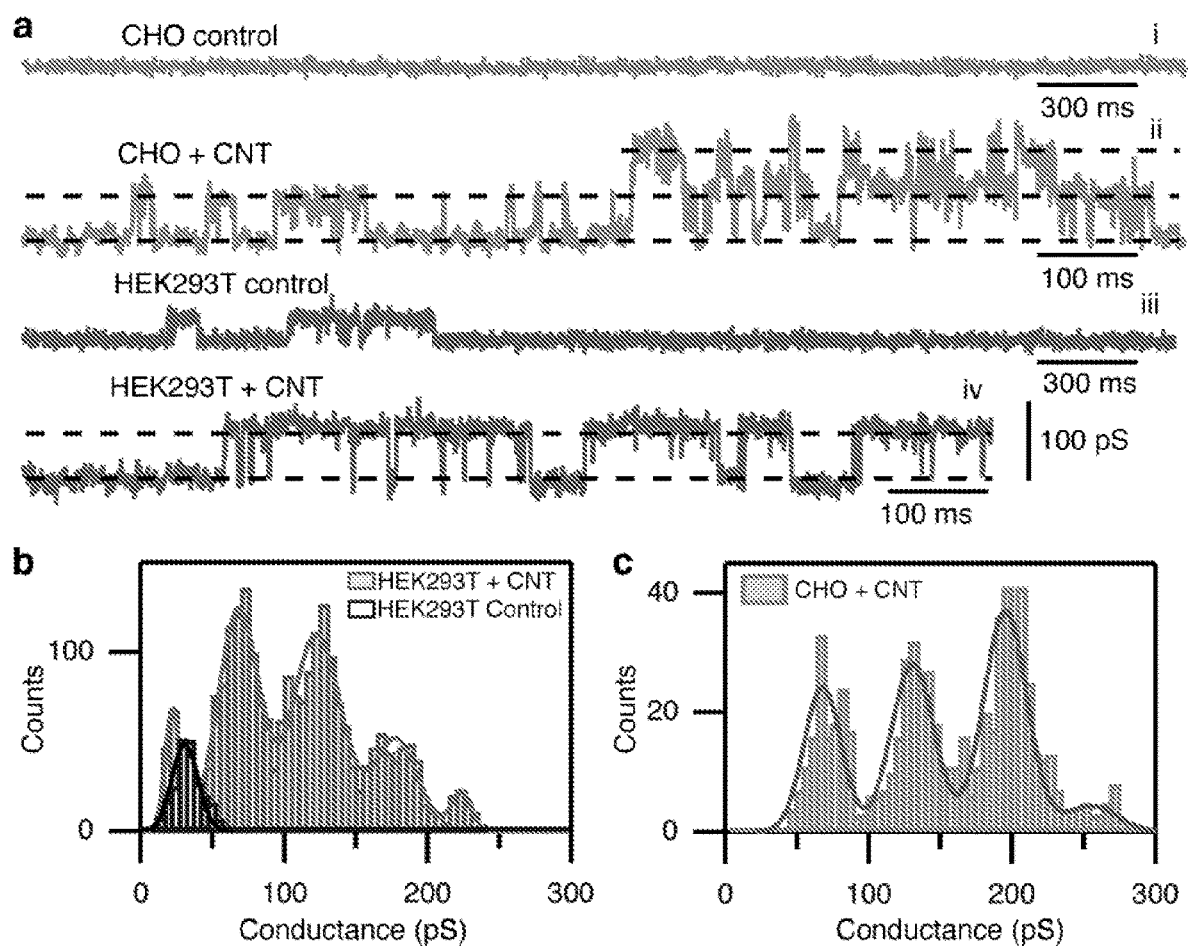
FIGS. 4A-4C: CNT porin incorporation into live cell membranes. A. Representative conductance traces for CNT porin incorporation and gating in CHO (ii) and HEK293T (iv) cells (−60 mV holding potential, 150 mM KCl). Traces (i, iii) were recorded in absence of CNT porins. Dashed lines added as guide to the eye. B, C. Histograms of conductance steps for CNT porin incorporation into (B) HEK293T (blue bars, n=2467, 13 cells) and (C) CHO (bars, n=657, 5 cells) cell membranes fitted to a sum of Gaussian peaks (solid lines). See Methods for peak positions. Native channel activity for HEK293T cells (black bars and black solid line, n=227, 5 cells) is also seen with CNT porins.
Figure 13:
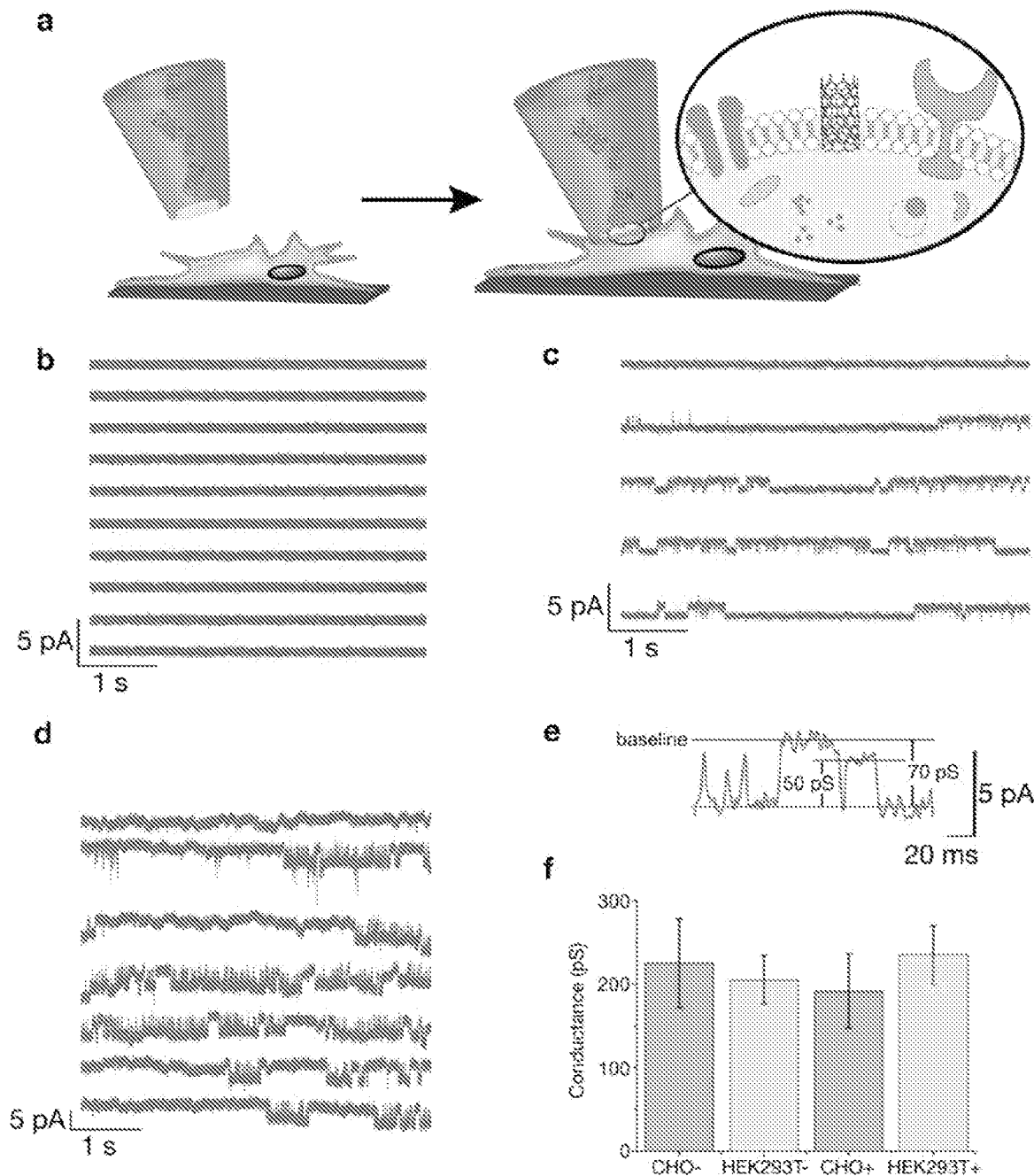
FIGS. 13A-13F: CNT porin conductance in cellular membranes.

Finally, patch-clamp measurements were used to demonstrate that CNT porins can spontaneously incorporate into the membranes of live Chinese hamster ovary (CHO) and Human embryonic kidney (HEK293T) cell lines. For both CHO cells (in 5 out of 6 trials) and HEK293T cells (in 13 out of 15 trials) Applicants detected channel-like activity emerging 60-90 s after the start of the recording (FIG. 4A and FIGS. 13A-13F). In both cases the dominant activity corresponded to a unitary conductance of approximately 70 pS (68.1±0.8 pS for HEK 293T cells and 67.6±1.4 pS for CHO cells) and its multiples (FIG. 4B, 4C, also see FIG. 13).

Control experiments performed without CNT porins in the patch pipette showed no endogenous channel activity in CHO cells (10 out of 10 cells). HEK293T cells showed endogenous channel activity with unitary conductance of 30.6±0.3 pS (FIG. 4B, FIG. 13C, 5 out of 5 cells), which was also present as 21.9±0.7 pS peak in the data obtained for interactions of HEK293T cells with CNT porins (FIG. 4B). Importantly, CNT porins incorporated into cell membranes display low-conductance sub-states (FIG. 13E), completely mimicking the conductance dynamics observed in planar lipid membranes.

Figure 14:
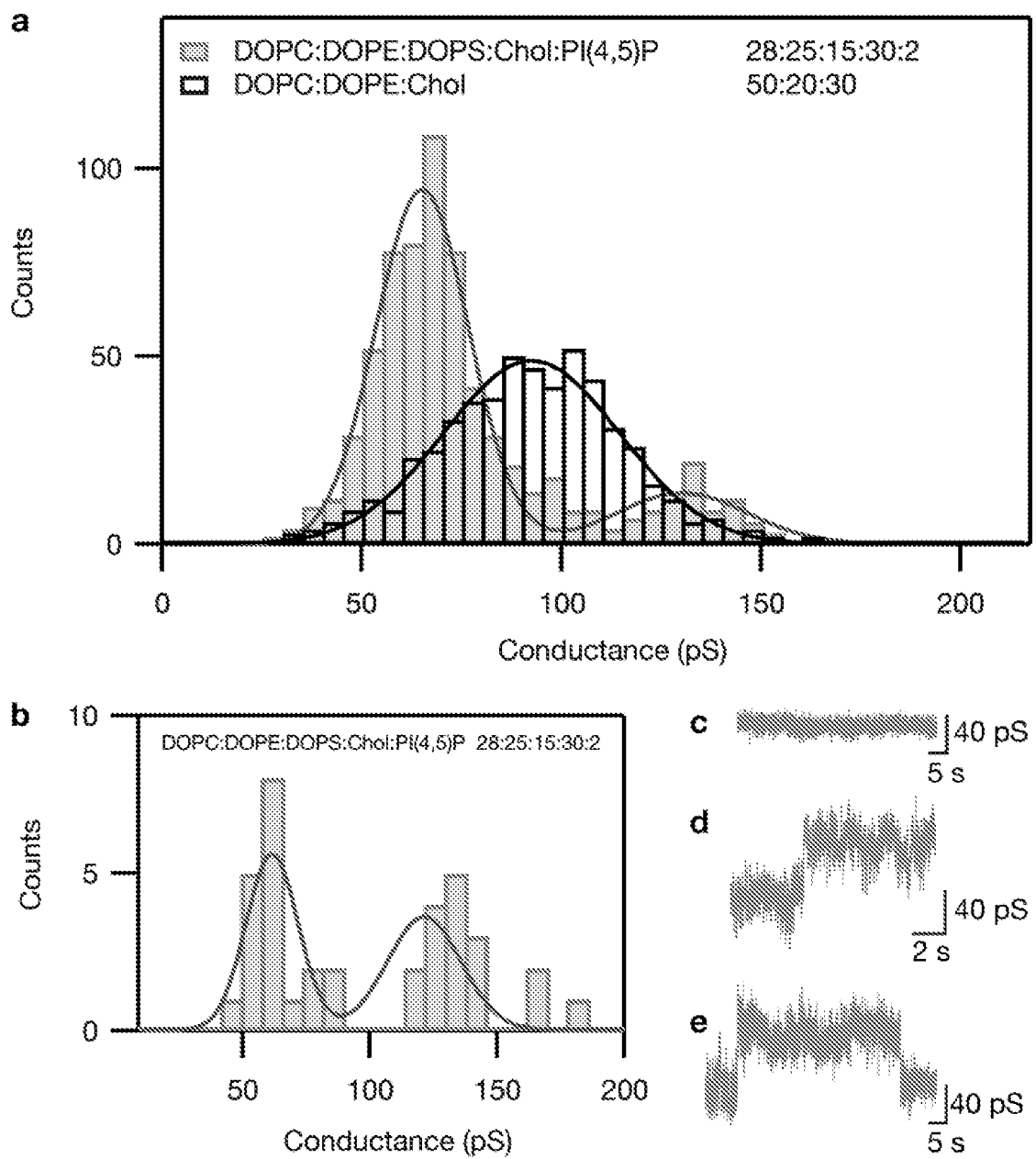
FIGS. 14A-14E: CNT porin conductance in patches isolated from planar lipid bilayers and giant unilamellar vesicles. A. Histogram of conductance values measured for CNT porin incorporation into a planar lipid bilayer mimicking the composition of a charged plasma membrane (light grey bars, n=681, 5 membranes, 3 controls without CNT porins showed no events) and a similar lipid bilayer without charged species (black bars, n=540, 5 membranes, 3 controls without CNT porins showed no events). The background electrolyte concentration was kept at 150 mM. Solid lines correspond to the fit of the data to a distribution expected for multiple channel incorporation. The primary peak positions are 65.1±0.4 pS (charged bilayer) and 92.5±0.6 pS (uncharged bilayer). B. Histogram of conductance values measured for CNT porins reconstituted into giant unilamellar vesicles (GUV) mimicking the composition of charged plasma membrane (bars, n=40, 3 membranes), Solid lines corresponds to the fit of the data to a distribution expected for multiple channel incorporation with the primary conductance peak at 60±2 pS. C. Representative control experiment demonstrating lack of spontaneous pore formation in the bilayer patch. D, E. Patch-clamp measurements of the CNT porin incorporation events in planar lipid bilayer (D) and GUV membrane (E).

Applicants detected similar single-channel activity using patch-clamp experiments on lipid bilayers, corroborating spontaneous incorporation of the CNT porins into the lipid membrane patch inside the patch-pipette. Notably, the unitary conductance detected in these experiments depended on the lipid composition (FIG. 14A). In charged membranes containing the core ingredients of the plasma membrane, the measured conductance was 64.7+/−0.5 pS (at 150 mM KCl), closely corresponding to the dominant unitary conductance detected in cellular membranes. Applicants observed similar conductances for CNT porins pre-reconstituted into giant unilamellar vesicles (FIGS. 14B, 14E), demonstrating that the activity of CNT porins does not depend on the membrane incorporation pathway. However, when Applicants excluded charged lipid species from the bilayer composition, the unitary conductance shifted to 92.5+/−0.6 pS (at 150 mM KCl). This conductance level corresponds to the conductance of 0.62 nS after correcting for the difference in electrolyte concentration (150 mM vs. 1M KCl), in excellent agreement with the value from the planar lipid bilayer experiments (FIG. 2C). The origins of the modulation in conductance caused by the membrane surface charge should be clarified by follow-up studies.

CNT porins represent a universal prototype of a synthetic membrane channel. Their inherent robustness towards biological and chemical challenges, and their exceptional biocompatibility gives CNT porins a significant advantage for bionanofluidic and cellular interface applications. Without being bound by theory, the modification of CNT porins with synthetic "gates" (28) could dramatically alter their selectivity for uses in synthetic cells, drug delivery, and biosensing.

While various illustrative embodiments of the invention are described above, it will be apparent to one skilled in the art that various changes and modifications may be made therein without departing from the invention. The appended claims are intended to cover all such changes and modifications that fall within the true scope of the apparatus and methods of the present invention.

REFERENCES

1. Sui, H. et al. Structural basis of water-specific transport through the AQP1 water channel. *Nature* 414, 872-878 (2001).
2. Langecker, M. et al. Synthetic Lipid Membrane Channels Formed by Designed DNA Nanostructures. *Science* 338, 932-936 (2012).
3. Li, J. et al. Ion-beam sculpting at nanometre length scales. *Nature* 412, 166-169 (2001).
4. Hinds, B. J. et al. Aligned multiwalled carbon nanotube membranes. *Science* 303, 62-65 (2004).
5. Liu, H. et al. Translocation of Single-Stranded DNA Through Single-Walled Carbon Nanotubes. *Science* 327, 64-67 (2010).
6. Lee, C. Y. et al. Coherence Resonance in a Single-Walled Carbon Nanotube Ion Channel. *Science* 329, 1320-1324 (2010).
7. Zimmerli, U. & Koumoutsakos, P. Simulations of Electrophoretic RNA Transport Through Transmembrane Carbon Nanotubes. *Biophys. J.* 94, 2546-2557 (2008).
8. Hummer, G. et al. Water conduction through the hydrophobic channel of a carbon nanotube. *Nature* 414, 188-190 (2001).
9. Lopez, C. F. et al. Understanding nature's design for a nanosyringe. *Proc. Natl. Acad. Sci. USA* 101, 4431-4434 (2004).
10. Dutt, M. J. et al. Interactions of End-functionalized Nanotubes with Lipid Vesicles: Spontaneous Insertion and Nanotube Self-Organization. *Curr. Nanosci.* 7, 699-715 (2011).
11. Lacerda, L. et al. How do functionalized carbon nanotubes land on, bind to and pierce through model and plasma membranes. *Nanoscale* 5, 10242-10250 (2013).
12. Kam, N. W. S. et al. Carbon nanotubes as multifunctional biological transporters and near-infrared agents for selective cancer cell destruction. *Proc. Natl. Acad. Sci. USA* 102, 11600-11605 (2005).
13. Liu, L. et al. Ultrashort single-walled carbon nanotubes in a lipid bilayer as a new nanopore sensor. *Nat. Commun.* 4 (2013).
14. Sun, X. et al. Optical Properties of Ultrashort Semiconducting Single-Walled Carbon Nanotube Capsules Down to Sub-10 nm. *J. Am. Chem. Soc.* 130, 6551-6555 (2008).
15. Le Duc, Y. et al. Imidazole-Quartet Water and Proton Dipolar Channels. *Angew. Chem. Int. Ed.* 50, 11366-11372 (2011).
16. Fornasiero, F. et al. Ion Exclusion by sub 2-nm Carbon Nanotube Pores. *Proc. Natl. Acad. Sci. USA* 105, 17250-17255 (2008).
17. Walther, J. H. et al. Barriers to Superfast Water Transport in Carbon Nanotube Membranes. *Nano Lett.* 13, 1910-1914 (2013).
18. Gu, L.-Q. & Bayley, H. Interaction of the Noncovalent Molecular Adapter, β-Cyclodextrin, with the Staphylococcal α-Hemolysin Pore. *Biophys. J.* 79, 1967-1975 (2000).
19. Nestorovich, E. M. et al. Residue ionization and ion transport through OmpF channels. *Biophys. J.* 85, 3718-3729 (2003).
20. Powell, M. R. et al. Nanoprecipitation-assisted ion current oscillations. *Nat. Nanotechnol.* 3, 51-57 (2007).
21. Powell, M. R. et al. Electric-field-induced wetting and dewetting in single hydrophobic nanopores. *Nat. Nanotechnol.* 6, 798-802 (2011).
22. Lev, A. et al. Rapid switching of ion current in narrow pores: implications for biological ion channels. *Proc. Roy. Soc. B* 252, 187-192 (1993).
23. Shimizu, S. et al. Stochastic Pore Blocking and Gating in PDMS—Glass Nanopores from Vapor—Liquid Phase Transitions. *J. Phys. Chem. C* 117, 9641-9651 (2013).
24. Buyukdagli, S. et al. Ionic Capillary Evaporation in Weakly Charged Nanopores. *Phys. Rev. Lett.* 105, 158103 (2010).
25. Kasianowicz, J. J. et al. Characterization of individual polynucleotide molecules using a membrane channel. *Proc. Natl. Acad. Sci. USA* 93, 13770-13773 (1996).
26. Hall, A. R. et al. Hybrid pore formation by directed insertion of α-haemolysin into solid-state nanopores. *Nat. Nanotechnol.* 5, 874-877 (2010).

27. Venkatesan, B. M. & Bashir, R. Nanopore sensors for nucleic acid analysis. *Nat. Nanotechnol.* 6, 615-624 (2011).
28. Majumder, M. et al. Effect of tip functionalization on transport through vertically oriented carbon nanotube membranes. *J. Am. Chem. Soc* 127, 9062-9070 (2005).
29. Hague, F. et al. Incorporation of a viral DNA-packaging motor channel in lipid bilayers for real-time, single-molecule sensing of chemicals and double-stranded DNA. *Nat. Protoc.* 8, 373-392 (2013).
30. Neher, E. et al. Ionic selectivity, saturation, and block in gramicidin A channels. *J. Membr. Biol.* 40, 97-116 (1978).
31. Frolov, V. A. et al. Shape bistability of a membrane neck: a toggle switch to control vesicle content release. *Proc. Natl. Acad. Sci.* 100, 8698-8703 (2003).
32. Shnyrova, A. V. et al. Geometric catalysis of membrane fission driven by flexible dynamin rings. *Science* 339, 1433-1436 (2013).
33. Edelstein, A. et al. Computer control of microscopes using μManager. *Curr. Protoc. Molec. Biol.*, Chapter: 14.20 (2010).
34. Geng, J. et al. Stochastic transport in carbon nanotube porins in lipid bilayters and live cell membranes. *Nature* 514, 612-615 (Oct. 29, 2014).

The invention claimed is:

1. A liposome vesicle comprising a lipid bilayer, wherein the lipid bilayer of the liposome vesicle comprises (a) one or more phospholipids and (b) lipid-coated nanotubes comprised of a material selected from carbon, molybdenum disulfide, or boron nitride and having an internal diameter of from about 0.5 nm to about 10 nm, and having a length greater than 5 nm to about 30 nm, wherein the length of the nanotubes is greater than a thickness of the lipid bilayer of the liposome vesicle and more than 50% of the nanotubes have an angle of 15 degrees or less with respect to a direction perpendicular to a plane of the lipid bilayer of the liposome vesicle and wherein the nanotubes form channels across the lipid bilayer of the liposome vesicle.

2. The liposome vesicle of claim 1, wherein the length of the nanotubes is greater than 5 nm to about 15 nm.

3. The liposome vesicle of claim 1, wherein the one or more phospholipids comprise at least one of 1,2-dioleoyl-sn-glycero-3-phosphocholine (DOPC), and 1,2-diphytanoyl-sn-glycero-3-phosphocholine (DPhPC).

4. The liposome vesicle of claim 1, further comprising a cargo moiety.

5. The liposome vesicle of claim 4, wherein the cargo moiety is selected from the group consisting of a small molecule drug, an imaging agent, or a polynucleotide.

6. The liposome vesicle of claim 4, wherein the cargo moiety is inside a lumen of the liposome vesicle.

7. A method of synthesizing a liposome vesicle of claim 1, comprising segmenting a nanotube into shorter segmented nanotubes in the presence of an effective amount of one or more phospholipids and self-assembling the segmented nanotubes and the one or more phospholipids to form a lipid bilayer of the liposome vesicle, wherein the lipid bilayer of the liposome vesicle comprises (a) the one or more phospholipids and the segmented nanotubes, wherein the segmented nanotubes comprise a material selected from carbon, molybdenum disulfide, or boron nitride and having an internal diameter of from about 0.5 nm to about 10 nm, and having a length greater than 5 nm to about 30 nm, wherein the length of the nanotubes is greater than a thickness of the lipid bilayer of the liposome vesicle and more than 50% of the nanotubes have an angle of 15 degrees or less with respect to a direction perpendicular to a plane of the lipid bilayer of the liposome vesicle.

8. The method of claim 7, wherein the segmenting is performed by ultrasonication.

9. The method of claim 7, wherein the one or more phospholipids comprise 1,2-dioleoyl-sn-glycero-3-phosphocholine (DOPC).

10. The method of claim 7, wherein the length of the segmented nanotubes is greater than 5 nm to about 15 nm.

11. The method of claim 7, wherein the one or more phospholipids comprise at least one of 1,2-dioleoyl-sn-glycero-3-phosphocholine (DOPC), and 1,2-diphytanoyl-sn-glycero-3-phosphocholine (DPhPC).

12. The liposome vesicle of claim 1, wherein the one or more phospholipids are selected from the group consisting of hydrogenated soy phosphatidylcholine (HSPC), lecithin, phosphatidylethanolamine, lysolecithin, lysophosphatidylethanolamine, phosphatidylserine, phosphatidylinositol, sphingomyelin, cephalin, cardiolipin, phosphatidic acid, cerebro sides, distearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimidomethyl)cyclohexane-1-carboxylate (DOPE-mal).

13. The liposome vesicle of claim 12, wherein the lipid bilayer of the liposome vesicle further comprises (c) one or more non-phosphorous containing lipids.

14. The liposome vesicle of claim 13, wherein the one or more non-phosphorous containing lipids are selected from the group consisting of stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, DDAB, DODAC, DMRIE, DMTAP, DOGS, DOTAP (DOTMA), DOSPA, DPTAP, DSTAP, and DC-Chol.

15. The liposome vesicle of claim 1, wherein the one or more phospholipids comprise 1,2-dioleoyl-sn-glycero-3-phosphocholine (DOPC).

16. The liposome vesicle of claim 15, wherein the lipid bilayer of the liposome vesicle further comprises 1,2-dioleoyl-sn-Glycero-3-Phosphoethanolamine (DOPE), and cholesterol (Choi).

17. The liposome vesicle of claim 16, wherein the lipid bilayer of the liposome vesicle further comprises 1,2-dioleoyl-sft-Glycero-3-Phospho-L-Serine (DOPS) and 1,2-dioleoyl-sn-Glycero-3-Phosphoinositol-4,5-Bisphosphate (PI(4,5)P2).

18. The liposome vesicle of claim 17, wherein the lipid bilayer further comprises 1,2-dioleoyl-sn-Glycero-3-Phosphoethanolamine-N-(Lissamine Pvhodamine B sulfonyl) (Rh-DOPE.

19. The liposome vesicle of claim 1, wherein the lipid bilayer of the liposome vesicle is a charged lipid bilayer.

20. The liposome vesicle of claim 1, wherein the lipid bilayer of the liposome vesicle is a non-charged lipid bilayer.

21. The liposome vesicle of claim 1, wherein the length of the nanotubes is from 6.5 nm to about 30 nm.

22. The liposome vesicle of claim 21, wherein at least 60% of the nanotubes have the angle of 15 degrees or less with respect to the direction perpendicular to the plane of the lipid bilayer of the liposome vesicle.

23. The liposome vesicle of claim 21, wherein the one or more phospholipids comprise at least one of 1,2-dioleoyl-sn-glycero-3-phosphocholine (DOPC), and 1,2-diphytanoyl-sn-glycero-3-phosphocholine (DPhPC).

24. The liposome vesicle of claim 1, wherein the length of the nanotubes is from 6.5 nm to about 15 nm.

25. The liposome vesicle of claim 24, wherein at least 60% of the nanotubes have the angle of 15 degrees or less with respect to the direction perpendicular to the plane of the lipid bilayer of the liposome vesicle.

26. The liposome vesicle of claim 24, wherein the one or more phospholipids comprise at least one of 1,2-dioleoyl-sn-glycero-3-phosphocholine (DOPC), and 1,2-diphytanoyl-sn-glycero-3-phosphocholine (DPhPC).

27. The liposome vesicle of claim 1, wherein at least 60% of the nanotubes have the angle of 15 degrees or less with respect to the direction perpendicular to the plane of the lipid bilayer of the liposome vesicle.

28. The liposome vesicles of claim 1, wherein the channels formed by the nanotubes are stable channels that provide transport of chemical species across the lipid bilayer of the liposome vesicle.

* * * * *